(12) United States Patent
Denenburg et al.

(10) Patent No.: US 10,806,667 B2
(45) Date of Patent: Oct. 20, 2020

(54) FLUID TRANSFER DEVICES FOR FILLING DRUG PUMP CARTRIDGES WITH LIQUID DRUG CONTENTS

(71) Applicant: West Pharma. Services IL, Ltd., Ra'anana (IL)

(72) Inventors: Igor Denenburg, Gedera (IL); Uri David, Nes Ziona (IL)

(73) Assignee: WEST PHARMA. SERVICES IL, LTD., Ra'anana (IL)

( * ) Notice: Subject to any disclaimer, the term of this patent is extended or adjusted under 35 U.S.C. 154(b) by 0 days.

(21) Appl. No.: 16/307,175

(22) PCT Filed: Jun. 5, 2017

(86) PCT No.: PCT/IL2017/050624
§ 371 (c)(1),
(2) Date: Dec. 5, 2018

(87) PCT Pub. No.: WO2017/212480
PCT Pub. Date: Dec. 14, 2017

(65) Prior Publication Data
US 2019/0117514 A1 Apr. 25, 2019

(30) Foreign Application Priority Data
Jun. 6, 2016 (IL) .......................... 246073

(51) Int. Cl.
*A61J 1/14* (2006.01)
*A61J 1/20* (2006.01)
*A61M 5/162* (2006.01)

(52) U.S. Cl.
CPC ........... *A61J 1/2072* (2015.05); *A61J 1/1406* (2013.01); *A61J 1/20* (2013.01); *A61J 1/201* (2015.05);
(Continued)

(58) Field of Classification Search
CPC .. A61J 1/1406; A61J 1/20; A61J 1/201; A61J 1/2017; A61J 1/2055; A61J 1/2072; A61J 1/2075; A61J 1/2096; A61M 5/162
See application file for complete search history.

(56) References Cited

U.S. PATENT DOCUMENTS

| 62,333 A | 2/1867 | Holl |
| 247,975 A | 10/1881 | Wickes |
(Continued)

FOREIGN PATENT DOCUMENTS

| CA | 2946559 A1 | 10/2015 |
| CN | 1636605 A | 7/2005 |
(Continued)

OTHER PUBLICATIONS

Int'l Search Report and Written Opinion dated Sep. 5, 2017 in Int'l Application No. PCT/IL2017/050624.
(Continued)

*Primary Examiner* — Kai H Weng
(74) *Attorney, Agent, or Firm* — Panitch Schwarze Belisario & Nadel LLP

(57) ABSTRACT

Fluid transfer devices for filling a drug pump cartridge with liquid drug contents for administration purposes. Fluid transfer device includes a dual open ended barrel partitioned by a transverse partition into a drug vial port for telescopic mounting on a drug vial and an open ended piston cylinder for slidingly receiving a piston head including a drug pump cartridge port for telescopic mounting on a leading cartridge end of a drug pump cartridge. Sliding insertion of the piston head into the piston cylinder to butt against the transverse partition urges air trapped in the compression chamber into the drug vial which in turn urges its liquid drug contents into the vented drug pump cartridge.

5 Claims, 13 Drawing Sheets

(52) U.S. Cl.
CPC ........... *A61J 1/2017* (2015.05); *A61J 1/2055* (2015.05); *A61J 1/2075* (2015.05); *A61J 1/2096* (2013.01); *A61M 5/162* (2013.01)

(56) References Cited

U.S. PATENT DOCUMENTS

| | | | |
|---|---|---|---|
| 254,444 A | 2/1882 | Vogel |
| 300,060 A | 6/1884 | Ford |
| 1,021,681 A | 3/1912 | Jennings |
| 1,704,817 A | 3/1929 | Ayers |
| 1,930,944 A | 10/1933 | Schmitz, Jr. |
| 2,326,490 A | 8/1943 | Perelson |
| 2,560,162 A | 7/1951 | Garwood |
| 2,748,769 A | 6/1956 | Huber |
| 2,830,587 A | 4/1958 | Everett |
| 2,931,668 A | 4/1960 | Baley |
| 2,968,497 A | 1/1961 | Treleman |
| 3,059,643 A | 10/1962 | Barton |
| D198,499 S | 6/1964 | Harautuneian |
| 3,225,763 A | 12/1965 | Waterman |
| 3,277,893 A | 10/1966 | Clark |
| 3,308,822 A | 3/1967 | De Luca |
| 3,484,849 A | 12/1969 | Huebner et al. |
| 3,618,637 A | 11/1971 | Santomieri |
| 3,757,981 A | 9/1973 | Harris, Sr. et al. |
| 3,782,365 A | 1/1974 | Pinna |
| 3,788,524 A | 1/1974 | Davis et al. |
| 3,822,700 A | 7/1974 | Pennington |
| 3,826,261 A | 7/1974 | Killinger |
| 3,872,992 A | 3/1975 | Larson |
| 3,885,607 A | 5/1975 | Peltier |
| 3,938,520 A | 2/1976 | Scislowicz et al. |
| 3,957,052 A | 5/1976 | Topham |
| 3,977,555 A | 8/1976 | Larson |
| 3,993,063 A | 11/1976 | Larrabee |
| 4,020,839 A | 5/1977 | Klapp |
| 4,026,128 A | 5/1977 | Blanco |
| 4,051,852 A | 10/1977 | Villari |
| D248,568 S | 7/1978 | Ismach |
| 4,109,670 A | 8/1978 | Slagel |
| 4,121,585 A | 10/1978 | Becker, Jr. |
| 4,161,178 A | 7/1979 | Genese |
| 4,187,848 A | 2/1980 | Taylor |
| D254,444 S | 3/1980 | Levine |
| 4,203,067 A | 5/1980 | Fitzky et al. |
| 4,203,443 A | 5/1980 | Genese |
| 4,210,173 A | 7/1980 | Choksi et al. |
| D257,286 S | 10/1980 | Folkman |
| 4,253,501 A | 3/1981 | Ogle |
| 4,296,786 A | 10/1981 | Brignola |
| 4,303,067 A | 12/1981 | Connolly et al. |
| 4,312,349 A | 1/1982 | Cohen |
| 4,314,586 A | 2/1982 | Folkman |
| 4,328,802 A | 5/1982 | Curley et al. |
| 4,335,717 A | 6/1982 | Bujan et al. |
| D267,199 S | 12/1982 | Koenig |
| 4,376,634 A | 3/1983 | Prior et al. |
| D268,871 S | 5/1983 | Benham et al. |
| 4,392,850 A | 7/1983 | Elias et al. |
| D270,282 S | 8/1983 | Gross |
| 4,410,321 A | 10/1983 | Pearson et al. |
| 4,411,662 A | 10/1983 | Pearson |
| D271,421 S | 11/1983 | Fetterman |
| 4,434,823 A | 3/1984 | Hudspith |
| 4,465,471 A | 8/1984 | Harris et al. |
| 4,475,915 A | 10/1984 | Sloane |
| 4,493,348 A | 1/1985 | Lemmons |
| 4,505,709 A | 3/1985 | Froning et al. |
| 4,507,113 A | 3/1985 | Dunlap |
| D280,018 S | 8/1985 | Scott |
| 4,532,969 A | 8/1985 | Kwaan |
| 4,564,054 A | 1/1986 | Gustavsson |
| 4,573,993 A | 3/1986 | Hoag et al. |
| 4,576,211 A | 3/1986 | Valentini et al. |
| 4,581,014 A | 4/1986 | Millerd et al. |
| 4,585,446 A | 4/1986 | Kempf |
| 4,588,396 A | 5/1986 | Stroebel et al. |
| 4,588,403 A | 5/1986 | Weiss et al. |
| D284,603 S | 7/1986 | Loignon |
| 4,604,093 A | 8/1986 | Brown et al. |
| 4,607,671 A | 8/1986 | Aalto et al. |
| 4,614,437 A | 9/1986 | Buehler |
| 4,638,975 A | 1/1987 | Iuchi et al. |
| 4,639,019 A | 1/1987 | Mittleman |
| 4,667,927 A | 5/1987 | Oscarsson |
| 4,675,020 A | 6/1987 | McPhee |
| 4,676,530 A | 6/1987 | Nordgren et al. |
| 4,683,975 A | 8/1987 | Booth et al. |
| 4,697,622 A | 10/1987 | Swift et al. |
| 4,721,133 A | 1/1988 | Sundblom |
| 4,729,401 A | 3/1988 | Raines |
| 4,735,608 A | 4/1988 | Sardam |
| 4,743,229 A | 5/1988 | Chu |
| 4,743,243 A | 5/1988 | Vaillancourt |
| 4,752,292 A | 6/1988 | Lopez et al. |
| 4,758,235 A | 7/1988 | Tu |
| 4,759,756 A | 7/1988 | Forman et al. |
| 4,778,447 A | 10/1988 | Velde et al. |
| 4,787,898 A | 11/1988 | Raines |
| 4,797,898 A | 1/1989 | Martinez |
| D300,060 S | 2/1989 | Molgaard-Nielsen |
| 4,804,366 A | 2/1989 | Zdeb et al. |
| 4,826,492 A | 5/1989 | Magasi |
| 4,832,690 A | 5/1989 | Kuu |
| 4,834,152 A | 5/1989 | Howson et al. |
| D303,013 S | 8/1989 | Konopka |
| 4,857,062 A | 8/1989 | Russell |
| 4,865,592 A | 9/1989 | Rycroft |
| 4,871,463 A | 10/1989 | Taylor et al. |
| 4,898,209 A | 2/1990 | Zbed |
| 4,909,290 A | 3/1990 | Coccia |
| 4,919,596 A | 4/1990 | Slate et al. |
| 4,927,423 A | 5/1990 | Malmborg |
| 4,931,040 A | 6/1990 | Haber et al. |
| 4,932,944 A | 6/1990 | Jagger et al. |
| 4,967,797 A | 11/1990 | Manska |
| D314,050 S | 1/1991 | Sone |
| D314,622 S | 2/1991 | Andersson et al. |
| 4,997,430 A | 3/1991 | Van der Heiden et al. |
| 5,006,114 A | 4/1991 | Rogers et al. |
| 5,035,686 A | 7/1991 | Crittenden et al. |
| 5,041,105 A | 8/1991 | D'Alo et al. |
| 5,045,066 A | 9/1991 | Scheuble et al. |
| 5,049,129 A | 9/1991 | Zdeb et al. |
| 5,053,015 A | 10/1991 | Gross |
| 5,061,248 A | 10/1991 | Sacco |
| 5,088,996 A | 2/1992 | Kopfer et al. |
| 5,096,575 A | 3/1992 | Cosack |
| 5,104,387 A | 4/1992 | Pokorney et al. |
| 5,113,904 A | 5/1992 | Aslanian |
| 5,122,124 A | 6/1992 | Novacek et al. |
| 5,125,908 A | 6/1992 | Cohen |
| 5,125,915 A | 6/1992 | Berry et al. |
| D328,788 S | 8/1992 | Sagae et al. |
| 5,171,230 A | 12/1992 | Eland et al. |
| 5,201,705 A | 4/1993 | Berglund et al. |
| 5,201,717 A | 4/1993 | Wyatt et al. |
| 5,203,771 A | 4/1993 | Melker et al. |
| 5,203,775 A | 4/1993 | Frank et al. |
| 5,211,638 A | 5/1993 | Dudar et al. |
| 5,232,029 A | 8/1993 | Knox et al. |
| 5,232,109 A | 8/1993 | Tirrell et al. |
| 5,242,432 A | 9/1993 | DeFrank |
| 5,247,972 A | 9/1993 | Tetreault |
| D341,420 S | 11/1993 | Conn |
| 5,269,768 A | 12/1993 | Cheung |
| 5,270,219 A | 12/1993 | DeCastro et al. |
| 5,279,576 A | 1/1994 | Loo et al. |
| 5,288,290 A | 2/1994 | Brody |
| 5,300,034 A | 4/1994 | Behnke et al. |
| 5,301,685 A | 4/1994 | Guirguis |
| 5,304,163 A | 4/1994 | Bonnici et al. |
| 5,304,165 A | 4/1994 | Haber et al. |
| 5,308,483 A | 5/1994 | Sklar et al. |

(56) References Cited

U.S. PATENT DOCUMENTS

| | | |
|---|---|---|
| 5,312,377 A | 5/1994 | Dalton |
| 5,328,474 A | 7/1994 | Raines |
| D349,648 S | 8/1994 | Tirrell et al. |
| 5,334,163 A | 8/1994 | Sinnett |
| 5,334,179 A | 8/1994 | Poli et al. |
| 5,342,346 A | 8/1994 | Honda et al. |
| 5,344,417 A | 9/1994 | Wadsworth, Jr. |
| 5,348,544 A | 9/1994 | Sweeney et al. |
| 5,348,548 A | 9/1994 | Meyer et al. |
| 5,350,372 A | 9/1994 | Ikeda et al. |
| 5,364,386 A | 11/1994 | Fukuoka et al. |
| 5,364,387 A | 11/1994 | Sweeney |
| 5,374,264 A | 12/1994 | Wadsworth, Jr. |
| 5,385,547 A | 1/1995 | Wong et al. |
| 5,397,303 A | 3/1995 | Sancoff et al. |
| D357,733 S | 4/1995 | Matkovich |
| 5,429,614 A | 7/1995 | Fowles et al. |
| 5,433,330 A | 7/1995 | Yatsko et al. |
| 5,445,630 A | 8/1995 | Richmond |
| 5,445,631 A | 8/1995 | Uchida |
| D362,718 S | 9/1995 | Deily et al. |
| 5,451,374 A | 9/1995 | Molina |
| 5,454,805 A | 10/1995 | Brony |
| 5,464,111 A | 11/1995 | Vacek et al. |
| 5,464,123 A | 11/1995 | Scarrow |
| 5,466,219 A | 11/1995 | Lynn et al. |
| 5,466,220 A | 11/1995 | Brenneman |
| 5,470,327 A | 11/1995 | Helgren et al. |
| 5,471,994 A | 12/1995 | Guirguis |
| 5,472,022 A | 12/1995 | Michel et al. |
| 5,478,337 A | 12/1995 | Okamoto et al. |
| 5,482,446 A | 1/1996 | Williamson et al. |
| 5,492,147 A | 2/1996 | Challender et al. |
| 5,496,274 A | 3/1996 | Graves et al. |
| D369,406 S | 4/1996 | Niedospial et al. |
| 5,505,714 A | 4/1996 | Dassa et al. |
| 5,509,433 A | 4/1996 | Paradis |
| 5,515,871 A | 5/1996 | Bittner et al. |
| 5,520,659 A | 5/1996 | Hedges |
| 5,526,853 A | 6/1996 | McPhee et al. |
| 5,527,306 A | 6/1996 | Raining |
| 5,531,695 A | 7/1996 | Swisher |
| 5,547,471 A | 8/1996 | Thompson et al. |
| 5,549,577 A | 8/1996 | Siegel et al. |
| 5,554,128 A | 9/1996 | Hedges |
| 5,562,686 A | 10/1996 | Sauer et al. |
| 5,562,696 A | 10/1996 | Nobles et al. |
| 5,566,729 A | 10/1996 | Grabenkort et al. |
| 5,569,191 A | 10/1996 | Meyer |
| 5,573,281 A | 11/1996 | Keller |
| 5,578,015 A | 11/1996 | Robb |
| 5,583,052 A | 12/1996 | Portnoff et al. |
| 5,584,819 A | 12/1996 | Kopfer |
| 5,591,143 A | 1/1997 | Trombley et al. |
| 5,603,706 A | 2/1997 | Wyatt et al. |
| 5,607,439 A | 3/1997 | Yoon |
| 5,611,576 A | 3/1997 | Guala |
| 5,616,203 A | 4/1997 | Stevens |
| 5,636,660 A | 6/1997 | Pfleiderer et al. |
| 5,637,101 A | 6/1997 | Shillington |
| 5,641,010 A | 6/1997 | Maier |
| 5,645,538 A | 7/1997 | Richmond |
| 5,647,845 A | 7/1997 | Haber et al. |
| 5,651,776 A | 7/1997 | Appling et al. |
| 5,653,686 A | 8/1997 | Coulter et al. |
| 5,658,133 A | 8/1997 | Anderson et al. |
| 5,672,160 A | 9/1997 | Osterlind et al. |
| 5,674,195 A | 10/1997 | Truthan |
| 5,676,346 A | 10/1997 | Leinsing |
| 5,685,845 A | 11/1997 | Grimard |
| D388,172 S | 12/1997 | Cipes |
| 5,699,821 A | 12/1997 | Paradis |
| 5,702,019 A | 12/1997 | Grimard |
| 5,718,346 A | 2/1998 | Weiler |
| 5,728,087 A | 3/1998 | Niedospial, Jr. |
| D393,722 S | 4/1998 | Fangrow, Jr. et al. |
| 5,738,144 A | 4/1998 | Rogers |
| 5,743,312 A | 4/1998 | Pfeifer et al. |
| 5,746,733 A | 5/1998 | Capaccio et al. |
| 5,752,942 A | 5/1998 | Doyle et al. |
| 5,755,696 A | 5/1998 | Caizza |
| 5,766,211 A | 6/1998 | Wood et al. |
| 5,772,630 A | 6/1998 | Ljungquist |
| 5,772,652 A | 6/1998 | Zielinski |
| RE35,841 E | 7/1998 | Frank et al. |
| 5,776,116 A | 7/1998 | Lopez et al. |
| 5,782,872 A | 7/1998 | Muller |
| 5,806,831 A | 9/1998 | Paradis |
| 5,810,792 A | 9/1998 | Fangrow, Jr. et al. |
| 5,814,020 A | 9/1998 | Gross |
| D399,559 S | 10/1998 | Molina |
| 5,817,082 A | 10/1998 | Niedospial, Jr. et al. |
| 5,820,621 A | 10/1998 | Yale et al. |
| 5,827,262 A | 10/1998 | Neftel et al. |
| 5,832,971 A | 11/1998 | Yale et al. |
| 5,833,213 A | 11/1998 | Ryan |
| 5,834,744 A | 11/1998 | Risman |
| 5,839,715 A | 11/1998 | Leinsing |
| 5,853,406 A | 12/1998 | Masuda et al. |
| D405,522 S | 2/1999 | Hoenig et al. |
| 5,868,710 A | 2/1999 | Battiato et al. |
| 5,871,110 A | 2/1999 | Grimard et al. |
| 5,873,872 A | 2/1999 | Thibault et al. |
| 5,879,337 A | 3/1999 | Kuracina et al. |
| 5,879,345 A | 3/1999 | Aneas |
| 5,887,633 A | 3/1999 | Yale et al. |
| 5,890,610 A | 4/1999 | Jansen et al. |
| 5,891,129 A | 4/1999 | Daubert et al. |
| 5,893,397 A | 4/1999 | Peterson et al. |
| 5,897,526 A | 4/1999 | Vaillancourt |
| 5,899,468 A | 5/1999 | Apps et al. |
| 5,902,280 A | 5/1999 | Powles et al. |
| 5,902,298 A | 5/1999 | Niedospial, Jr. et al. |
| D410,740 S | 6/1999 | Molina |
| 5,911,710 A | 6/1999 | Barry et al. |
| 5,919,182 A | 7/1999 | Avallone |
| 5,921,419 A | 7/1999 | Niedospial, Jr. et al. |
| 5,924,584 A | 7/1999 | Hellstrom et al. |
| 5,925,029 A | 7/1999 | Jansen et al. |
| 5,935,112 A | 8/1999 | Stevens et al. |
| 5,941,848 A | 8/1999 | Nishimoto et al. |
| 5,941,850 A | 8/1999 | Shah et al. |
| 5,944,700 A | 8/1999 | Nguyen et al. |
| 5,954,104 A | 9/1999 | Daubert et al. |
| 5,968,022 A | 10/1999 | Saito |
| 5,971,181 A | 10/1999 | Niedospial, Jr. et al. |
| 5,971,965 A | 10/1999 | Mayer |
| 5,989,237 A | 11/1999 | Fowles et al. |
| 6,003,566 A | 12/1999 | Thibault et al. |
| 6,004,278 A | 12/1999 | Botich et al. |
| 6,019,750 A | 2/2000 | Fowles et al. |
| 6,022,339 A | 2/2000 | Fowles et al. |
| 6,036,171 A | 3/2000 | Weinheimer et al. |
| 6,039,093 A | 3/2000 | Mrotzek et al. |
| 6,039,302 A | 3/2000 | Cote, Sr. et al. |
| D422,357 S | 4/2000 | Niedospial, Jr. et al. |
| 6,063,068 A | 5/2000 | Fowles et al. |
| D427,308 S | 6/2000 | Zinger |
| D427,309 S | 6/2000 | Molina |
| 6,070,623 A | 6/2000 | Aneas |
| 6,071,270 A | 6/2000 | Fowles et al. |
| 6,080,132 A | 6/2000 | Cole et al. |
| D428,141 S | 7/2000 | Brotspies et al. |
| 6,086,762 A | 7/2000 | Guala |
| 6,089,541 A | 7/2000 | Weinheimer et al. |
| 6,090,091 A | 7/2000 | Fowles et al. |
| 6,090,093 A | 7/2000 | Thibault et al. |
| 6,092,692 A | 7/2000 | Riskin |
| D430,291 S | 8/2000 | Jansen et al. |
| 6,099,511 A | 8/2000 | Devos |
| 6,113,068 A | 9/2000 | Ryan |
| 6,113,583 A | 9/2000 | Fowles et al. |
| 6,117,114 A | 9/2000 | Paradis |
| D431,864 S | 10/2000 | Jansen |

(56) References Cited

U.S. PATENT DOCUMENTS

| | | |
|---|---|---|
| 6,139,534 A | 10/2000 | Niedospial, Jr. et al. |
| 6,142,446 A | 11/2000 | Leinsing |
| 6,146,362 A | 11/2000 | Turnbull et al. |
| 6,149,623 A | 11/2000 | Reynolds |
| 6,156,025 A | 12/2000 | Niedospial, Jr. et al. |
| 6,159,192 A | 12/2000 | Fowles et al. |
| 6,168,037 B1 | 1/2001 | Grimard |
| 6,171,287 B1 | 1/2001 | Lynn et al. |
| 6,171,293 B1 | 1/2001 | Rowley et al. |
| 6,173,852 B1 | 1/2001 | Browne |
| 6,173,868 B1 | 1/2001 | DeJonge |
| 6,174,304 B1 | 1/2001 | Weston |
| 6,179,822 B1 | 1/2001 | Niedospial, Jr. |
| 6,179,823 B1 | 1/2001 | Niedospial, Jr. |
| 6,186,997 B1 | 2/2001 | Gabbard et al. |
| 6,206,861 B1 | 3/2001 | Mayer |
| 6,221,041 B1 | 4/2001 | Russo |
| 6,221,054 B1 | 4/2001 | Martin et al. |
| 6,221,065 B1 | 4/2001 | Davis |
| 6,238,372 B1 | 5/2001 | Zinger et al. |
| 6,245,044 B1 | 6/2001 | Daw et al. |
| D445,501 S | 7/2001 | Niedospial, Jr. |
| D445,895 S | 7/2001 | Svendsen |
| 6,253,804 B1 | 7/2001 | Safabash |
| 6,258,078 B1 | 7/2001 | Thilly |
| 6,280,430 B1 | 8/2001 | Neftel et al. |
| 6,290,688 B1 | 9/2001 | Lopez et al. |
| 6,296,621 B1 | 10/2001 | Masuda et al. |
| 6,299,131 B1 | 10/2001 | Ryan |
| 6,343,629 B1 | 2/2002 | Wessman et al. |
| 6,348,044 B1 | 2/2002 | Coletti et al. |
| 6,358,236 B1 | 3/2002 | DeFoggi et al. |
| 6,364,866 B1 | 4/2002 | Furr et al. |
| 6,378,576 B2 | 4/2002 | Thibault et al. |
| 6,378,714 B1 | 4/2002 | Jansen et al. |
| 6,379,340 B1 | 4/2002 | Zinger et al. |
| D457,954 S | 5/2002 | Wallace et al. |
| 6,382,442 B1 | 5/2002 | Thibault et al. |
| 6,386,397 B2 | 5/2002 | Brotspies et al. |
| 6,408,897 B1 | 6/2002 | Laurent et al. |
| 6,409,708 B1 | 6/2002 | Wessman |
| 6,440,107 B1 | 8/2002 | Trombley, III et al. |
| 6,453,949 B1 | 9/2002 | Chau |
| 6,453,956 B2 | 9/2002 | Safabash |
| 6,474,375 B2 | 11/2002 | Spero et al. |
| 6,478,788 B1 | 11/2002 | Aneas |
| D468,015 S | 12/2002 | Horppu |
| 6,499,617 B1 | 12/2002 | Niedospial, Jr. et al. |
| 6,503,240 B1 | 1/2003 | Niedospial, Jr. et al. |
| 6,503,244 B2 | 1/2003 | Hayman |
| 6,520,932 B2 | 2/2003 | Taylor |
| 6,524,278 B1 | 2/2003 | Campbell et al. |
| 6,524,295 B2 | 2/2003 | Daubert et al. |
| D472,316 S | 3/2003 | Douglas et al. |
| 6,530,903 B2 | 3/2003 | Wang et al. |
| 6,537,263 B1 | 3/2003 | Aneas |
| D472,630 S | 4/2003 | Douglas et al. |
| 6,544,246 B1 | 4/2003 | Niedospial, Jr. |
| 6,551,299 B2 | 4/2003 | Miyoshi et al. |
| 6,558,365 B2 | 5/2003 | Zinger et al. |
| 6,571,837 B2 | 6/2003 | Jansen et al. |
| 6,572,591 B2 | 6/2003 | Mayer |
| 6,575,955 B2 | 6/2003 | Azzolini |
| 6,581,593 B1 | 6/2003 | Rubin et al. |
| 6,582,415 B1 | 6/2003 | Fowles et al. |
| D476,731 S | 7/2003 | Cise et al. |
| 6,591,876 B2 | 7/2003 | Safabash |
| 6,599,273 B1 | 7/2003 | Lopez |
| 6,601,721 B2 | 8/2003 | Jansen et al. |
| 6,626,309 B1 | 9/2003 | Jansen et al. |
| 6,632,201 B1 | 10/2003 | Mathias et al. |
| 6,638,244 B1 | 10/2003 | Reynolds |
| D482,121 S | 11/2003 | Harding et al. |
| D482,447 S | 11/2003 | Harding et al. |
| 6,651,956 B2 | 11/2003 | Miller |
| 6,652,509 B1 | 11/2003 | Helgren et al. |
| D483,487 S | 12/2003 | Harding et al. |
| D483,869 S | 12/2003 | Tran et al. |
| 6,656,433 B2 | 12/2003 | Sasso |
| 6,666,852 B2 | 12/2003 | Niedospial, Jr. |
| 6,681,810 B2 | 1/2004 | Weston |
| 6,681,946 B1 | 1/2004 | Jansen et al. |
| 6,682,509 B2 | 1/2004 | Lopez |
| 6,692,478 B1 | 2/2004 | Paradis |
| 6,692,829 B2 | 2/2004 | Stubler et al. |
| 6,695,829 B2 | 2/2004 | Hellstrom et al. |
| 6,699,229 B2 | 3/2004 | Zinger et al. |
| 6,706,022 B1 | 3/2004 | Leinsing et al. |
| 6,706,031 B2 | 3/2004 | Manera |
| 6,715,520 B2 | 4/2004 | Andreasson et al. |
| 6,729,370 B2 | 5/2004 | Norton et al. |
| 6,736,798 B2 | 5/2004 | Ohkubo et al. |
| 6,745,998 B2 | 6/2004 | Doyle |
| 6,746,438 B1 | 6/2004 | Amissolle |
| 6,752,180 B2 | 6/2004 | Delay |
| D495,416 S | 8/2004 | Dimeo et al. |
| D496,457 S | 9/2004 | Prais et al. |
| 6,802,490 B2 | 10/2004 | Leinsing et al. |
| 6,832,994 B2 | 12/2004 | Niedospial, Jr. et al. |
| 6,852,103 B2 | 2/2005 | Fowles et al. |
| 6,875,203 B1 | 4/2005 | Fowles et al. |
| 6,875,205 B2 | 4/2005 | Leinsing |
| 6,878,131 B2 | 4/2005 | Novacek et al. |
| 6,884,253 B1 | 4/2005 | McFarlane |
| 6,890,328 B2 | 5/2005 | Fowles et al. |
| D506,256 S | 6/2005 | Miyoshi et al. |
| 6,901,975 B2 | 6/2005 | Aramata et al. |
| 6,945,417 B2 | 9/2005 | Jansen et al. |
| 6,948,522 B2 | 9/2005 | Newbrough et al. |
| 6,949,086 B2 | 9/2005 | Ferguson et al. |
| 6,951,613 B2 | 10/2005 | Reif et al. |
| 6,957,745 B2 | 10/2005 | Thibault et al. |
| 6,960,164 B2 | 11/2005 | O'Heeron |
| 6,972,002 B2 | 12/2005 | Thorne |
| 6,979,318 B1 | 12/2005 | McDonald et al. |
| RE38,996 E | 2/2006 | Crawford et al. |
| 6,994,315 B2 | 2/2006 | Ryan et al. |
| 6,997,916 B2 | 2/2006 | Simas, Jr. et al. |
| 6,997,917 B2 | 2/2006 | Niedospial, Jr. et al. |
| 7,024,968 B2 | 4/2006 | Raudabough et al. |
| 7,070,589 B2 | 7/2006 | Lolachi et al. |
| 7,074,216 B2 | 7/2006 | Fowles et al. |
| 7,083,600 B2 | 8/2006 | Meloul |
| 7,086,431 B2 | 8/2006 | D'Antonio et al. |
| 7,097,637 B2 | 8/2006 | Triplett et al. |
| 7,100,890 B2 | 9/2006 | Cote, Sr. et al. |
| 7,140,401 B2 | 11/2006 | Wilcox et al. |
| 7,150,735 B2 | 12/2006 | Hickle |
| 7,192,423 B2 | 3/2007 | Wong |
| 7,195,623 B2 | 3/2007 | Burroughs et al. |
| 7,241,285 B1 | 7/2007 | Dikeman |
| 7,294,122 B2 | 11/2007 | Kubo et al. |
| 7,306,199 B2 | 12/2007 | Leinsing et al. |
| D561,348 S | 2/2008 | Zinger et al. |
| 7,326,188 B1 | 2/2008 | Russell et al. |
| 7,326,194 B2 | 2/2008 | Zinger et al. |
| 7,350,764 B2 | 4/2008 | Raybuck |
| 7,354,422 B2 | 4/2008 | Riesenberger et al. |
| 7,354,427 B2 | 4/2008 | Fangrow |
| 7,425,209 B2 | 9/2008 | Fowles et al. |
| 7,435,246 B2 | 10/2008 | Zihlmann |
| D580,558 S | 11/2008 | Shigesada et al. |
| 7,452,348 B2 | 11/2008 | Hasegawa |
| 7,470,257 B2 | 12/2008 | Norton et al. |
| 7,470,265 B2 | 12/2008 | Brugger et al. |
| 7,472,932 B2 | 1/2009 | Weber et al. |
| 7,488,297 B2 | 2/2009 | Flaherty |
| 7,491,197 B2 | 2/2009 | Jansen et al. |
| 7,497,848 B2 | 3/2009 | Leinsing et al. |
| 7,523,967 B2 | 4/2009 | Steppe |
| 7,530,546 B2 | 5/2009 | Ryan et al. |
| D595,420 S | 6/2009 | Suzuki et al. |
| D595,421 S | 6/2009 | Suzuki et al. |
| 7,540,863 B2 | 6/2009 | Haindl |

(56) References Cited

U.S. PATENT DOCUMENTS

| | | |
|---|---|---|
| 7,540,865 B2 | 6/2009 | Griffin et al. |
| 7,544,191 B2 | 6/2009 | Peluso et al. |
| D595,862 S | 7/2009 | Suzuki et al. |
| D595,863 S | 7/2009 | Suzuki et al. |
| 7,611,487 B2 | 11/2009 | Woehr et al. |
| 7,611,502 B2 | 11/2009 | Daly |
| 7,615,041 B2 | 11/2009 | Sullivan et al. |
| 7,628,779 B2 | 12/2009 | Aneas |
| 7,632,261 B2 | 12/2009 | Zinger et al. |
| D608,900 S | 1/2010 | Giraud et al. |
| 7,654,995 B2 | 2/2010 | Warren et al. |
| 7,670,326 B2 | 3/2010 | Shemesh |
| 7,695,445 B2 | 4/2010 | Yuki |
| 7,704,229 B2 | 4/2010 | Moberg et al. |
| D616,090 S | 5/2010 | Kawamura |
| 7,713,247 B2 | 5/2010 | Lopez |
| 7,717,886 B2 | 5/2010 | Lopez |
| 7,722,090 B2 | 5/2010 | Burton et al. |
| D616,984 S | 6/2010 | Gilboa |
| 7,731,678 B2 | 6/2010 | Tennican et al. |
| 7,743,799 B2 | 6/2010 | Mosier et al. |
| 7,744,581 B2 | 6/2010 | Wallen et al. |
| 7,757,901 B2 | 7/2010 | Welp |
| 7,758,082 B2 | 7/2010 | Weigel et al. |
| 7,758,560 B2 | 7/2010 | Connell et al. |
| 7,762,524 B2 | 7/2010 | Cawthon et al. |
| 7,766,304 B2 | 8/2010 | Phillips |
| 7,771,383 B2 | 8/2010 | Truitt |
| D624,641 S | 9/2010 | Boclet |
| 7,799,009 B2 | 9/2010 | Niedospial, Jr. et al. |
| 7,803,140 B2 | 9/2010 | Fangrow, Jr. |
| D627,216 S | 11/2010 | Fulginiti |
| D630,732 S | 1/2011 | Lev et al. |
| 7,862,537 B2 | 1/2011 | Zinger et al. |
| 7,867,215 B2 | 1/2011 | Akerlund et al. |
| 7,879,018 B2 | 2/2011 | Zinger et al. |
| 7,883,499 B2 | 2/2011 | Fangrow |
| 7,895,216 B2 | 2/2011 | Longshaw et al. |
| D634,007 S | 3/2011 | Zinger et al. |
| 7,900,659 B2 | 3/2011 | Whitley et al. |
| D637,713 S | 5/2011 | Nord et al. |
| 7,963,954 B2 | 6/2011 | Kavazov |
| D641,080 S | 7/2011 | Zinger et al. |
| 7,985,216 B2 | 7/2011 | Daily et al. |
| D644,104 S | 8/2011 | Maeda et al. |
| 3,007,461 A1 | 8/2011 | Huo et al. |
| 7,993,328 B2 | 8/2011 | Whitley |
| 8,012,132 B2 | 9/2011 | Lum et al. |
| 8,016,809 B2 | 9/2011 | Zinger et al. |
| 8,021,325 B2 | 9/2011 | Zinger et al. |
| 8,025,653 B2 | 9/2011 | Capitaine et al. |
| 8,025,683 B2 | 9/2011 | Morrison |
| 8,029,472 B2 | 10/2011 | Leinsing et al. |
| 8,038,123 B2 | 10/2011 | Ruschke et al. |
| 8,066,688 B2 | 11/2011 | Zinger et al. |
| 8,070,739 B2 | 12/2011 | Zinger et al. |
| 8,075,550 B2 | 12/2011 | Nord et al. |
| 8,096,525 B2 | 1/2012 | Ryan |
| 8,105,314 B2 | 1/2012 | Fangrow, Jr. |
| D654,166 S | 2/2012 | Lair |
| D655,017 S | 2/2012 | Mosler et al. |
| 8,122,923 B2 | 2/2012 | Kraus et al. |
| 8,123,736 B2 | 2/2012 | Kraushaar et al. |
| D655,071 S | 3/2012 | Davila |
| D657,461 S | 4/2012 | Schembre et al. |
| 8,152,779 B2 | 4/2012 | Cabiri |
| 8,157,784 B2 | 4/2012 | Rogers |
| 8,167,863 B2 | 5/2012 | Yow |
| 8,172,824 B2 | 5/2012 | Pfeifer et al. |
| 8,177,768 B2 | 5/2012 | Leinsing |
| 8,182,452 B2 | 5/2012 | Mansour et al. |
| 8,187,248 B2 | 5/2012 | Zihlmann |
| 8,196,614 B2 | 6/2012 | Kriheli |
| 8,197,459 B2 | 6/2012 | Jansen et al. |
| 8,211,069 B2 | 7/2012 | Fangrow, Jr. |
| 8,225,959 B2 | 7/2012 | Lambrecht |
| 8,241,268 B2 | 8/2012 | Whitley |
| 8,262,628 B2 | 9/2012 | Fangrow, Jr. |
| 8,262,641 B2 | 9/2012 | Vedrine et al. |
| 8,267,127 B2 | 9/2012 | Kriheli |
| D669,980 S | 10/2012 | Lev et al. |
| 8,287,513 B2 | 10/2012 | Ellstrom et al. |
| 8,328,784 B2 | 12/2012 | Jensen et al. |
| D673,673 S | 1/2013 | Wang |
| D674,084 S | 1/2013 | Linnenschmidt |
| D674,088 S | 1/2013 | Lev et al. |
| 8,348,898 B2 | 1/2013 | Cabiri |
| D681,230 S | 4/2013 | Mosler et al. |
| 8,454,573 B2 | 6/2013 | Wyatt et al. |
| 8,469,939 B2 | 6/2013 | Fangrow, Jr. |
| 8,475,404 B2 | 7/2013 | Foshee et al. |
| 8,480,645 B1 | 7/2013 | Choudhury et al. |
| 8,480,646 B2 | 7/2013 | Nord et al. |
| 8,506,548 B2 | 8/2013 | Okiyama |
| 8,511,352 B2 | 8/2013 | Kraus et al. |
| 8,512,309 B2 | 8/2013 | Shemesh et al. |
| D690,009 S | 9/2013 | Schembre et al. |
| D690,418 S | 9/2013 | Rosenquist |
| 8,523,837 B2 | 9/2013 | Wiggins et al. |
| 8,545,476 B2 | 10/2013 | Ariagno et al. |
| 8,551,067 B2 | 10/2013 | Zinger et al. |
| 8,556,879 B2 | 10/2013 | Okiyama |
| 8,562,582 B2 | 10/2013 | Tuckwell et al. |
| 8,608,723 B2 | 12/2013 | Lev et al. |
| 8,628,508 B2 | 1/2014 | Weitzel et al. |
| 8,636,689 B2 | 1/2014 | Halili, Jr. et al. |
| 8,684,992 B2 | 4/2014 | Sullivan et al. |
| 8,684,994 B2 | 4/2014 | Lev et al. |
| 8,752,598 B2 | 6/2014 | Denenburg et al. |
| D714,935 S | 10/2014 | Nishioka et al. |
| D717,406 S | 11/2014 | Stanley et al. |
| D717,948 S | 11/2014 | Strong et al. |
| D719,650 S | 12/2014 | Arinobe et al. |
| D720,067 S | 12/2014 | Rosenquist |
| D720,451 S | 12/2014 | Denenburg et al. |
| D720,452 S | 12/2014 | Jordan |
| 8,900,212 B2 | 12/2014 | Kubo |
| 8,905,994 B1 | 12/2014 | Lev et al. |
| 8,915,882 B2 | 12/2014 | Cabiri |
| D720,850 S | 1/2015 | Hsia et al. |
| D732,660 S | 6/2015 | Ohashi |
| D732,664 S | 6/2015 | Woehr et al. |
| D733,291 S | 6/2015 | Wang |
| D733,292 S | 6/2015 | Rogers |
| D733,293 S | 6/2015 | Rogers |
| 9,072,827 B2 | 7/2015 | Cabiri |
| D738,494 S | 9/2015 | Kashmirian |
| D741,457 S | 10/2015 | Guest |
| 9,149,575 B2 | 10/2015 | Cabiri |
| D750,235 S | 2/2016 | Maurice |
| 9,254,242 B2 | 2/2016 | Mueller et al. |
| D757,933 S | 5/2016 | Lev et al. |
| 9,339,438 B2 | 5/2016 | Lev et al. |
| 9,393,365 B2 | 7/2016 | Cabiri |
| 9,414,991 B2 | 8/2016 | Sanders et al. |
| 9,486,391 B2 | 11/2016 | Shemesh |
| 9,492,610 B2 | 11/2016 | Cabiri |
| 9,511,190 B2 | 12/2016 | Cabiri |
| 9,522,234 B2 | 12/2016 | Cabiri |
| D794,183 S | 8/2017 | Lev et al. |
| 9,763,855 B2 | 9/2017 | Fangrow |
| 9,801,786 B2 | 10/2017 | Lev et al. |
| 10,206,854 B2 | 2/2019 | Wu et al. |
| 10,376,654 B2 | 8/2019 | Sanders et al. |
| 2001/0000347 A1 | 4/2001 | Hellstrom et al. |
| 2001/0025671 A1 | 10/2001 | Safabash |
| 2001/0029360 A1 | 10/2001 | Miyoshi et al. |
| 2001/0051793 A1 | 12/2001 | Weston |
| 2002/0017328 A1 | 2/2002 | Loo |
| 2002/0055711 A1 | 5/2002 | Lavi et al. |
| 2002/0065488 A1 | 5/2002 | Suzuki et al. |
| 2002/0066715 A1 | 6/2002 | Niedospial |
| 2002/0087118 A1 | 7/2002 | Reynolds et al. |
| 2002/0087141 A1 | 7/2002 | Zinger et al. |

(56) References Cited

U.S. PATENT DOCUMENTS

| | | |
|---|---|---|
| 2002/0087144 A1 | 7/2002 | Zinger et al. |
| 2002/0104584 A1 | 8/2002 | Spero et al. |
| 2002/0115980 A1 | 8/2002 | Niedospial et al. |
| 2002/0121496 A1 | 9/2002 | Thiebault et al. |
| 2002/0123736 A1 | 9/2002 | Fowles et al. |
| 2002/0127150 A1 | 9/2002 | Sasso |
| 2002/0128628 A1 | 9/2002 | Fathallah |
| 2002/0138045 A1 | 9/2002 | Moen |
| 2002/0173752 A1 | 11/2002 | Polzin |
| 2002/0193777 A1 | 12/2002 | Aneas |
| 2003/0028156 A1 | 2/2003 | Juliar |
| 2003/0036725 A1 | 2/2003 | Lavi et al. |
| 2003/0068354 A1 | 4/2003 | Reif et al. |
| 2003/0069550 A1 | 4/2003 | Sharp |
| 2003/0073971 A1 | 4/2003 | Saker |
| 2003/0100866 A1 | 5/2003 | Reynolds |
| 2003/0109846 A1 | 6/2003 | Zinger |
| 2003/0120209 A1 | 6/2003 | Jensen et al. |
| 2003/0135159 A1 | 7/2003 | Daily et al. |
| 2003/0153895 A1 | 8/2003 | Leinsing |
| 2003/0187420 A1 | 10/2003 | Akerlund et al. |
| 2003/0191445 A1 | 10/2003 | Wallen et al. |
| 2003/0195479 A1 | 10/2003 | Kuracina et al. |
| 2003/0199827 A1 | 10/2003 | Thorne |
| 2003/0199846 A1 | 10/2003 | Fowles et al. |
| 2003/0199847 A1 | 10/2003 | Akerlund et al. |
| 2003/0205843 A1 | 11/2003 | Adams |
| 2003/0236543 A1 | 12/2003 | Brenneman et al. |
| 2004/0010207 A1 | 1/2004 | Flaherty et al. |
| 2004/0024354 A1 | 2/2004 | Reynolds |
| 2004/0039365 A1 | 2/2004 | Aramata et al. |
| 2004/0044327 A1 | 3/2004 | Hasegawa |
| 2004/0073189 A1 | 4/2004 | Wyatt et al. |
| 2004/0143218 A1 | 7/2004 | Das |
| 2004/0143226 A1 | 7/2004 | Marsden |
| 2004/0153047 A1 | 8/2004 | Blank et al. |
| 2004/0158172 A1 | 8/2004 | Hancock |
| 2004/0162540 A1 | 8/2004 | Walenciak et al. |
| 2004/0167472 A1 | 8/2004 | Howell et al. |
| 2004/0181192 A1 | 9/2004 | Cuppy |
| 2004/0186424 A1 | 9/2004 | Hjertman |
| 2004/0199139 A1 | 10/2004 | Fowles et al. |
| 2004/0204699 A1 | 10/2004 | Hanly et al. |
| 2004/0217315 A1 | 11/2004 | Doyle |
| 2004/0225274 A1 | 11/2004 | Jansen et al. |
| 2004/0236305 A1 | 11/2004 | Jansen et al. |
| 2004/0249341 A1 | 12/2004 | Newbrough et al. |
| 2004/0255952 A1 | 12/2004 | Carlsen et al. |
| 2005/0015070 A1 | 1/2005 | Delnevo et al. |
| 2005/0016626 A1 | 1/2005 | Wilcox et al. |
| 2005/0049553 A1 | 3/2005 | Triplett et al. |
| 2005/0055008 A1 | 3/2005 | Paradis et al. |
| 2005/0082828 A1 | 4/2005 | Wicks et al. |
| 2005/0124964 A1 | 6/2005 | Niedospial et al. |
| 2005/0137523 A1 | 6/2005 | Wyatt et al. |
| 2005/0137566 A1 | 6/2005 | Fowles et al. |
| 2005/0148994 A1 | 7/2005 | Leinsing |
| 2005/0159706 A1 | 7/2005 | Wilkinson et al. |
| 2005/0159724 A1 | 7/2005 | Enerson |
| 2005/0182383 A1 | 8/2005 | Wallen |
| 2005/0209554 A1 | 9/2005 | Landau |
| 2005/0261637 A1 | 11/2005 | Miller |
| 2005/0277896 A1 | 12/2005 | Messerli et al. |
| 2006/0030832 A1 | 2/2006 | Niedospial et al. |
| 2006/0079834 A1 | 4/2006 | Tennican et al. |
| 2006/0089594 A1 | 4/2006 | Landau |
| 2006/0089603 A1 | 4/2006 | Truitt et al. |
| 2006/0095015 A1 | 5/2006 | Hobbs et al. |
| 2006/0106360 A1 | 5/2006 | Wong |
| 2006/0135948 A1 | 6/2006 | Varma |
| 2006/0155257 A1 | 7/2006 | Reynolds |
| 2006/0161192 A1 | 7/2006 | Young |
| 2006/0173410 A1 | 8/2006 | Moberg et al. |
| 2006/0178646 A1 | 8/2006 | Harris et al. |
| 2006/0195029 A1 | 8/2006 | Shults et al. |
| 2006/0212004 A1 | 9/2006 | Atil |
| 2006/0253084 A1 | 11/2006 | Nordgren |
| 2006/0259004 A1 | 11/2006 | Connell et al. |
| 2007/0016381 A1 | 1/2007 | Kamath et al. |
| 2007/0024995 A1 | 2/2007 | Hayashi |
| 2007/0060904 A1 | 3/2007 | Vedrine et al. |
| 2007/0078428 A1 | 4/2007 | Reynolds et al. |
| 2007/0079894 A1 | 4/2007 | Kraus et al. |
| 2007/0083164 A1 | 4/2007 | Barrelle et al. |
| 2007/0088252 A1 | 4/2007 | Pestotnik et al. |
| 2007/0088293 A1 | 4/2007 | Fangrow |
| 2007/0088313 A1 | 4/2007 | Zinger et al. |
| 2007/0106218 A1 | 5/2007 | Yodfat et al. |
| 2007/0106244 A1* | 5/2007 | Mosler ............... A61J 1/2096 604/411 |
| 2007/0112324 A1 | 5/2007 | Harnedi-Sangsari |
| 2007/0156112 A1 | 7/2007 | Walsh |
| 2007/0167904 A1 | 7/2007 | Zinger et al. |
| 2007/0167912 A1 | 7/2007 | Causey et al. |
| 2007/0191760 A1 | 8/2007 | Iguchi et al. |
| 2007/0191764 A1 | 8/2007 | Zihlmann |
| 2007/0191767 A1 | 8/2007 | Hennessy et al. |
| 2007/0203451 A1 | 8/2007 | Murakami et al. |
| 2007/0219483 A1 | 9/2007 | Kitani et al. |
| 2007/0244447 A1 | 10/2007 | Capitaine et al. |
| 2007/0244461 A1 | 10/2007 | Fangrow |
| 2007/0244462 A1 | 10/2007 | Fangrow |
| 2007/0244463 A1 | 10/2007 | Warren et al. |
| 2007/0249995 A1 | 10/2007 | Van Manen |
| 2007/0255202 A1 | 11/2007 | Kitani et al. |
| 2007/0265574 A1 | 11/2007 | Tennican et al. |
| 2007/0265581 A1 | 11/2007 | Funamura et al. |
| 2007/0270778 A9 | 11/2007 | Zinger et al. |
| 2007/0287953 A1 | 12/2007 | Ziv et al. |
| 2007/0299404 A1 | 12/2007 | Katoh et al. |
| 2008/0009789 A1 | 1/2008 | Zinger et al. |
| 2008/0009822 A1 | 1/2008 | Enerson |
| 2008/0015496 A1 | 1/2008 | Hamedi-Sangsari |
| 2008/0132851 A1 | 6/2008 | Shaw et al. |
| 2008/0135051 A1 | 6/2008 | Lee |
| 2008/0172024 A1 | 7/2008 | Yow |
| 2008/0188799 A1 | 8/2008 | Mueller-Beckhaus et al. |
| 2008/0195049 A1 | 8/2008 | Thalmann et al. |
| 2008/0208138 A1 | 8/2008 | Lim |
| 2008/0215015 A1 | 9/2008 | Cindrich et al. |
| 2008/0249473 A1 | 10/2008 | Ruth et al. |
| 2008/0249479 A1 | 10/2008 | Zinger et al. |
| 2008/0249498 A1 | 10/2008 | Fangrow |
| 2008/0262465 A1 | 10/2008 | Zinger et al. |
| 2008/0269687 A1 | 10/2008 | Chong |
| 2008/0275407 A1 | 11/2008 | Scheurer |
| 2008/0287905 A1 | 11/2008 | Hiejima et al. |
| 2008/0294100 A1 | 11/2008 | de Costa et al. |
| 2008/0306439 A1 | 12/2008 | Nelson et al. |
| 2008/0312634 A1 | 12/2008 | Helmerson |
| 2009/0012492 A1 | 1/2009 | Zihlmann |
| 2009/0043253 A1 | 2/2009 | Podaima |
| 2009/0054834 A1 | 2/2009 | Zinger et al. |
| 2009/0054852 A1 | 2/2009 | Takano et al. |
| 2009/0062767 A1 | 3/2009 | Van Antwerp et al. |
| 2009/0076360 A1 | 3/2009 | Brister et al. |
| 2009/0082750 A1 | 3/2009 | Denenburg |
| 2009/0139724 A1 | 6/2009 | Gray et al. |
| 2009/0143758 A1 | 6/2009 | Okiyama |
| 2009/0177177 A1 | 7/2009 | Zinger et al. |
| 2009/0177178 A1 | 7/2009 | Pedersen |
| 2009/0187140 A1 | 7/2009 | Racz |
| 2009/0216103 A1 | 8/2009 | Brister et al. |
| 2009/0216212 A1 | 8/2009 | Fangrow, Jr. |
| 2009/0267011 A1 | 10/2009 | Hatton |
| 2009/0299325 A1 | 12/2009 | Vedrine et al. |
| 2009/0318946 A1 | 12/2009 | Tamesada |
| 2009/0326506 A1 | 12/2009 | Hasegawa et al. |
| 2010/0010443 A1 | 1/2010 | Morgan et al. |
| 2010/0016811 A1 | 1/2010 | Smith |
| 2010/0022985 A1 | 1/2010 | Sullivan et al. |
| 2010/0030181 A1 | 2/2010 | Helle et al. |
| 2010/0036319 A1 | 2/2010 | Drake et al. |
| 2010/0076397 A1 | 3/2010 | Reed et al. |

(56) References Cited

U.S. PATENT DOCUMENTS

| | | |
|---|---|---|
| 2010/0087786 A1 | 4/2010 | Zinger et al. |
| 2010/0137827 A1 | 6/2010 | Warren et al. |
| 2010/0137831 A1 | 6/2010 | Tsals |
| 2010/0152658 A1 | 6/2010 | Hanson et al. |
| 2010/0160889 A1 | 6/2010 | Smith et al. |
| 2010/0162548 A1 | 7/2010 | Leidig |
| 2010/0168664 A1 | 7/2010 | Zinger et al. |
| 2010/0168712 A1 | 7/2010 | Tuckwell et al. |
| 2010/0179506 A1 | 7/2010 | Shemesh et al. |
| 2010/0198148 A1 | 8/2010 | Zinger |
| 2010/0204670 A1 | 8/2010 | Kraushaar et al. |
| 2010/0228220 A1 | 9/2010 | Zinger et al. |
| 2010/0241088 A1 | 9/2010 | Ranalletta et al. |
| 2010/0274184 A1 | 10/2010 | Chun |
| 2010/0274202 A1 | 10/2010 | Hyde et al. |
| 2010/0286661 A1 | 11/2010 | Raday et al. |
| 2010/0312220 A1 | 12/2010 | Kalitzki |
| 2011/0004143 A1 | 1/2011 | Beiriger et al. |
| 2011/0004184 A1 | 1/2011 | Proksch et al. |
| 2011/0044850 A1 | 2/2011 | Solomon et al. |
| 2011/0054440 A1 | 3/2011 | Lewis |
| 2011/0087164 A1 | 4/2011 | Mosler et al. |
| 2011/0125056 A1 | 5/2011 | Merchant |
| 2011/0144584 A1 | 6/2011 | Wozencroft |
| 2011/0160655 A1 | 6/2011 | Hanson et al. |
| 2011/0160701 A1 | 6/2011 | Wyatt et al. |
| 2011/0172636 A1 | 7/2011 | Aasmul |
| 2011/0175347 A1 | 7/2011 | Okiyama |
| 2011/0218511 A1 | 9/2011 | Yokoyama |
| 2011/0224640 A1 | 9/2011 | Kuhn et al. |
| 2011/0230856 A1 | 9/2011 | Kyle et al. |
| 2011/0264037 A1 | 10/2011 | Foshee et al. |
| 2011/0264069 A1 | 10/2011 | Bochenko |
| 2011/0276007 A1 | 11/2011 | Denenburg |
| 2011/0319827 A1 | 12/2011 | Leinsing et al. |
| 2012/0022344 A1 | 1/2012 | Kube |
| 2012/0022469 A1 | 1/2012 | Alpert |
| 2012/0053555 A1 | 3/2012 | Ariagno et al. |
| 2012/0059332 A1 | 3/2012 | Woehr et al. |
| 2012/0059346 A1 | 3/2012 | Sheppard et al. |
| 2012/0067429 A1 | 3/2012 | Mosler et al. |
| 2012/0071819 A1 | 3/2012 | Bruggemann et al. |
| 2012/0078214 A1 | 3/2012 | Finke et al. |
| 2012/0123382 A1* | 5/2012 | Kubo .................. A61J 1/2096 604/413 |
| 2012/0184938 A1 | 7/2012 | Lev et al. |
| 2012/0215182 A1 | 8/2012 | Mansour et al. |
| 2012/0220977 A1 | 8/2012 | Yow |
| 2012/0220978 A1 | 8/2012 | Lev |
| 2012/0265163 A1 | 10/2012 | Cheng et al. |
| 2012/0271229 A1 | 10/2012 | Lev et al. |
| 2012/0296307 A1 | 11/2012 | Holt et al. |
| 2012/0310203 A1 | 12/2012 | Khaled et al. |
| 2012/0323172 A1 | 12/2012 | Lev et al. |
| 2012/0323187 A1 | 12/2012 | Iwase et al. |
| 2012/0323210 A1 | 12/2012 | Lev et al. |
| 2013/0046269 A1 | 2/2013 | Lev et al. |
| 2013/0053814 A1 | 2/2013 | Mueller-Beckhaus et al. |
| 2013/0096493 A1 | 4/2013 | Kubo et al. |
| 2013/0110049 A1 | 5/2013 | Cronenberg et al. |
| 2013/0144248 A1 | 6/2013 | Putter et al. |
| 2013/0199669 A1 | 8/2013 | Moy et al. |
| 2013/0226100 A1 | 8/2013 | Lev |
| 2013/0231630 A1 | 9/2013 | Kraus et al. |
| 2013/0237904 A1 | 9/2013 | Deneburg et al. |
| 2013/0253448 A1 | 9/2013 | Baron et al. |
| 2013/0289530 A1 | 10/2013 | Wyatt et al. |
| 2014/0020793 A1 | 1/2014 | Denenburg et al. |
| 2014/0096862 A1 | 4/2014 | Aneas |
| 2014/0150911 A1 | 6/2014 | Hanner et al. |
| 2014/0194854 A1 | 7/2014 | Tsals |
| 2014/0221940 A1 | 8/2014 | Clauson et al. |
| 2014/0277052 A1 | 9/2014 | Haselby et al. |
| 2014/0352845 A1 | 12/2014 | Lev et al. |
| 2015/0082746 A1 | 3/2015 | Ivosevic et al. |
| 2015/0088078 A1 | 3/2015 | Lev et al. |
| 2015/0112297 A1 | 4/2015 | Lev et al. |
| 2015/0290390 A1 | 10/2015 | Ring et al. |
| 2015/0297839 A1 | 10/2015 | Sanders et al. |
| 2015/0305770 A1 | 10/2015 | Fill et al. |
| 2016/0088995 A1 | 3/2016 | Ueda et al. |
| 2016/0166824 A1 | 6/2016 | Lev et al. |
| 2016/0199569 A1 | 7/2016 | Yevmenenko et al. |
| 2016/0228644 A1 | 8/2016 | Cabiri |
| 2016/0287475 A1 | 10/2016 | Yevmenenko et al. |
| 2016/0367439 A1 | 12/2016 | Davis et al. |
| 2019/0133885 A1 | 5/2019 | Wu et al. |

FOREIGN PATENT DOCUMENTS

| | | |
|---|---|---|
| CN | 1747683 A | 3/2006 |
| CN | 1863566 A | 11/2006 |
| CN | 1950049 A | 4/2007 |
| CN | 101001661 A | 7/2007 |
| CN | 101687083 A | 3/2010 |
| DE | 1064693 B | 9/1959 |
| DE | 1913926 A1 | 9/1970 |
| DE | 4122476 A1 | 1/1993 |
| DE | 0637443 A1 | 2/1995 |
| DE | 1408498 A1 | 5/1995 |
| DE | 19504413 A1 | 8/1996 |
| DE | 202004012714 U1 | 11/2004 |
| DE | 102007046951 B3 | 2/2009 |
| DE | 202009011019 U1 | 12/2010 |
| EM | 000627237-0001 | 1/2007 |
| EM | 001680703-0002 | 3/2010 |
| EP | 0192661 A1 | 9/1986 |
| EP | 0195018 A1 | 9/1986 |
| EP | 0258913 A2 | 3/1988 |
| EP | 0426403 A1 | 5/1991 |
| EP | 0282545 B1 | 2/1992 |
| EP | 0518397 A1 | 12/1992 |
| EP | 0416454 A1 | 1/1993 |
| EP | 0521460 A1 | 1/1993 |
| EP | 582038 A2 | 2/1994 |
| EP | 0598918 A1 | 6/1994 |
| EP | 0737467 A1 | 10/1996 |
| EP | 761562 A1 | 3/1997 |
| EP | 765652 A1 | 4/1997 |
| EP | 765853 A1 | 4/1997 |
| EP | 0806597 A1 | 11/1997 |
| EP | 829248 A2 | 3/1998 |
| EP | 0856331 A2 | 8/1998 |
| EP | 882441 A2 | 12/1998 |
| EP | 0887085 A2 | 12/1998 |
| EP | 0887885 A2 | 12/1998 |
| EP | 897708 A2 | 2/1999 |
| EP | 0898951 A2 | 3/1999 |
| EP | 960616 A2 | 12/1999 |
| EP | 1008337 A1 | 6/2000 |
| EP | 1029526 A1 | 8/2000 |
| EP | 1034809 A1 | 9/2000 |
| EP | 1051988 A2 | 11/2000 |
| EP | 0814866 A1 | 7/2003 |
| EP | 1323403 A1 | 7/2003 |
| EP | 1329210 A1 | 7/2003 |
| EP | 1396250 A1 | 3/2004 |
| EP | 1454609 A1 | 9/2004 |
| EP | 1454650 A1 | 9/2004 |
| EP | 1498097 A2 | 1/2005 |
| EP | 1872824 A1 | 1/2008 |
| EP | 1911432 A1 | 4/2008 |
| EP | 1919432 A1 | 5/2008 |
| EP | 1930038 A2 | 6/2008 |
| EP | 2090278 A1 | 8/2009 |
| EP | 2351548 A1 | 8/2011 |
| EP | 2351549 A1 | 8/2011 |
| EP | 2462913 A1 | 6/2012 |
| EP | 2512399 A1 | 10/2012 |
| FR | 2029242 A5 | 10/1970 |
| FR | 2856660 A1 | 12/2004 |
| FR | 2869795 A1 | 11/2005 |
| FR | 2931363 A1 | 11/2009 |
| GB | 1444210 A | 7/1976 |

(56) References Cited

FOREIGN PATENT DOCUMENTS

| | | |
|---|---|---|
| IL | 171662 | 10/2005 |
| IL | 186290 | 1/2008 |
| JP | 03-062426 B | 9/1991 |
| JP | 0282545 B1 | 2/1992 |
| JP | 06-050656 U | 7/1994 |
| JP | H08-000710 A | 1/1996 |
| JP | 09-104460 A | 4/1997 |
| JP | 09-104461 A | 4/1997 |
| JP | 10-118158 | 5/1998 |
| JP | H10-504736 A | 5/1998 |
| JP | 11503627 | 3/1999 |
| JP | 11-319031 A | 11/1999 |
| JP | 2000-508934 A | 7/2000 |
| JP | 2000-237278 A | 9/2000 |
| JP | 2000262497 A | 9/2000 |
| JP | 2001-505083 A | 4/2001 |
| JP | 2002-035140 A | 2/2002 |
| JP | 2002-516160 A | 6/2002 |
| JP | 2002-355318 A | 12/2002 |
| JP | 2003-033441 A | 2/2003 |
| JP | 2003-102807 A | 4/2003 |
| JP | 2004-501721 A | 1/2004 |
| JP | 2004-097253 A | 4/2004 |
| JP | 2004-522541 A | 7/2004 |
| JP | 2005-270629 A | 10/2005 |
| JP | 200661421 A | 3/2006 |
| JP | 2008-220961 A | 9/2008 |
| JP | 4329954 B2 | 9/2009 |
| JP | 2010063622 A | 3/2010 |
| JP | 2010-179128 A | 8/2010 |
| JP | 2012-205769 A | 10/2012 |
| JP | 2014000220 A | 1/2014 |
| WO | 8601712 A1 | 3/1986 |
| WO | 8605683 A1 | 10/1986 |
| WO | 9003536 A1 | 4/1990 |
| WO | 9403373 A1 | 2/1994 |
| WO | 9507066 A1 | 3/1995 |
| WO | 9513785 A1 | 5/1995 |
| WO | 9600053 A1 | 1/1996 |
| WO | 9609083 A1 | 3/1996 |
| WO | 9629113 A1 | 9/1996 |
| WO | 9736636 A1 | 10/1997 |
| WO | 9832411 A1 | 7/1998 |
| WO | 9837854 A1 | 9/1998 |
| WO | 9961093 A1 | 12/1999 |
| WO | 0128490 A1 | 4/2001 |
| WO | 0130425 A1 | 5/2001 |
| WO | 0132524 A1 | 5/2001 |
| WO | 0160311 A1 | 8/2001 |
| WO | 0189607 A2 | 11/2001 |
| WO | 0191693 A2 | 12/2001 |
| WO | 0202165 A2 | 1/2002 |
| WO | 200209797 A1 | 2/2002 |
| WO | 0232372 A1 | 4/2002 |
| WO | 0236191 A2 | 5/2002 |
| WO | 02066100 A2 | 8/2002 |
| WO | 02089900 A1 | 11/2002 |
| WO | 03051423 A2 | 6/2003 |
| WO | 03070147 A1 | 8/2003 |
| WO | 03079956 A1 | 10/2003 |
| WO | 2004041148 A1 | 5/2004 |
| WO | 2004096113 A2 | 11/2004 |
| WO | 2005002492 A1 | 1/2005 |
| WO | 2005018703 A2 | 3/2005 |
| WO | 2005041846 A2 | 5/2005 |
| WO | 2005105014 A2 | 11/2005 |
| WO | 2006099441 A2 | 9/2006 |
| WO | 2007015233 A1 | 2/2007 |
| WO | 2007017868 A1 | 2/2007 |
| WO | 2007052252 A1 | 5/2007 |
| WO | 2007/105221 A1 | 9/2007 |
| WO | 2007101772 A1 | 9/2007 |
| WO | 2008076459 A1 | 6/2008 |
| WO | 2008081424 A2 | 7/2008 |
| WO | 2008126090 A1 | 10/2008 |
| WO | 2009026443 A2 | 2/2009 |
| WO | 2009029010 A1 | 3/2009 |
| WO | 2009038860 A2 | 3/2009 |
| WO | 2009040804 A2 | 4/2009 |
| WO | 2009087572 A1 | 7/2009 |
| WO | 2009093249 A1 | 7/2009 |
| WO | 2009112489 A1 | 9/2009 |
| WO | 2009146088 A1 | 12/2009 |
| WO | 2010061743 A1 | 6/2010 |
| WO | 2010078227 A1 | 7/2010 |
| WO | 2010117580 A1 | 10/2010 |
| WO | 2011/004360 A1 | 1/2011 |
| WO | 2011039747 A1 | 4/2011 |
| WO | 2011058545 A1 | 5/2011 |
| WO | 2011058548 A1 | 5/2011 |
| WO | 2011077434 A1 | 6/2011 |
| WO | 2011090955 A1 | 7/2011 |
| WO | 2011104711 A1 | 9/2011 |
| WO | 2011156373 A1 | 12/2011 |
| WO | 2012/004790 A2 | 1/2012 |
| WO | 2012004784 A1 | 1/2012 |
| WO | 2012063230 A1 | 5/2012 |
| WO | 2012143921 A1 | 10/2012 |
| WO | 2012150587 A1 | 11/2012 |
| WO | 2013127813 A1 | 9/2013 |
| WO | 2013134246 A1 | 9/2013 |
| WO | 2013148435 A1 | 10/2013 |
| WO | 2013156944 A1 | 10/2013 |
| WO | 2013156994 A1 | 10/2013 |
| WO | 2014033706 A2 | 3/2014 |
| WO | 2014033710 A1 | 3/2014 |
| WO | 2014099395 A1 | 6/2014 |
| WO | 2014170888 A1 | 10/2014 |
| WO | 2014174278 A1 | 10/2014 |
| WO | 2016023590 A1 | 2/2016 |

OTHER PUBLICATIONS

Summit International Medical Technologies Inc., Vial Direct to Bag Spike 2020.

Merchant "An engineered control device for needle free reconstitution and transfer of compounded sterile intravenous drug solutions for immediate use to assist in complying with United States Pharmacopeia Chapter <797> standard", Adv Care, 2 pages, 2018.

Grifols Vial Adapter Product Literature, 2 pages, Jan. 2002. cited by other.

Novel Transfer, Mixing and Drug Delivery Systems, MOP Medimop Medical Projects Ltd. Catalog, 4 pages Rev. 4, 2004. cited by other.

Smart Site.RTM. Alaris Medical Systems Product Brochure, 4 pages, Issue 1, Oct. 1999. cited by other.

MixJect, downloaded from webpage: http://www.westpharma.com/en/products/pp./Mixject.aspx, Download Date: Aug. 8, 2012, 1 page.

MixJet Product Information Sheet, downloaded from webpage: http://www.westpharma.com/SiteCollectionDocuments/Recon/mixject%20product%20sheet.pdf; 1 page.

Silicone Rubber Overview Downloaded from webpage: http://www.knovel.com/web/portal/browse/display?_EXT_KNOVEL_DISPLAY_bookid=1023&VerticalID=0 on Sep. 2, 2011, Download Date: Sep. 2, 2011, Original Posting Date: 2010, 6 pages.

Kipp, "Plastic Material Data Sheets," retrieved from the Internet: http://www.knovel.com/web/portal/browse/display?_EXT_KNOVEL_DISPLAY_bookid=1023&VerticalID=0, retrieved on Feb. 9, 2011.

Alaris Medical Systems Product Brochure, 4 pages, Issue 1, Oct. 11, 1999.

Smart Site Needle-Free Systems, Alaris Medical Systems Webpage, 4 pages, Feb. 2006.

Photographs of Alaris Medical Systems SmartSite.RTM. device, 5 pages, 2002.

Non-Vented Vial Access Pin with Ultrasite.RTM. Valve, B. Braun Medical, Inc. website and product description, 3 pages, Feb. 2006.

IV disposables sets catalogue, Cardinal Health, Alaris® products, SmartSite® access devices and accessories product No. 10013365, SmartSite add-on bag access device with spike adapter and needle-free valve bag access port, pp. 1-5, Fall edition (2007).

(56) References Cited

OTHER PUBLICATIONS

Article with picture of West Pharmaceutical Services' Vial2Bag Needleless System, [on-line]; !Sips Newsletter, Oct. 26, 2007]; retrieved from Internet Feb. 16, 2010]; URL:<http://www.isips.org/reports/ISIPS_Newsletter_October_26_2007. html.> (7 pages. see pp. 5-6).

West, Vial2Bag Dc system, Oct. 2, 2014, https://web.archive.org/web/20141002065133/http://www.westpharma.com/en/products/pp./Reconstitutionsystems.aspx.

Vial2Bag DC, downloaded from webpage: https://www.youtube.com/watch?v=FEOkgIxNBrs, Original posting date: Aug. 21, 2014, 1 page.

Vial-Mate Adapter Device, Baxter, May 2017, downloaded from web page:http://www.baxtermedicationdeliveryproducts.com/drug-delivery/vialmate.html, Download Date: Jul. 28, 2017, original posting date: unknown, 1page.

\* cited by examiner

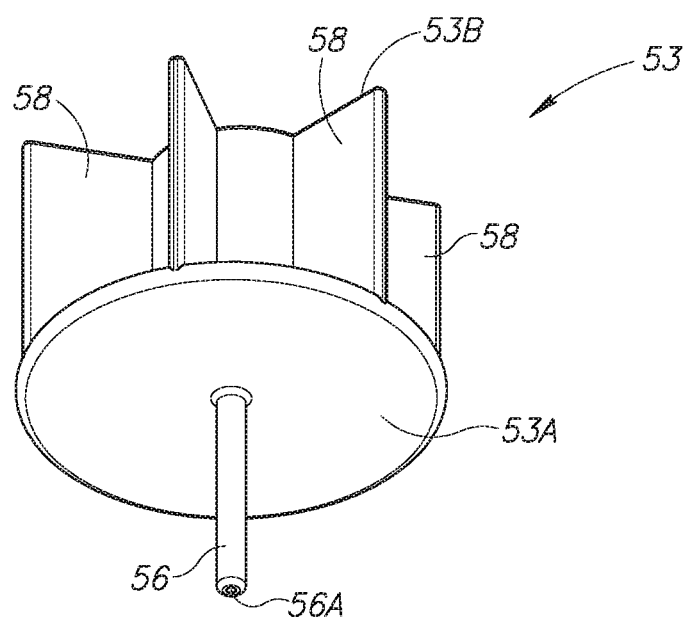
FIG. 6
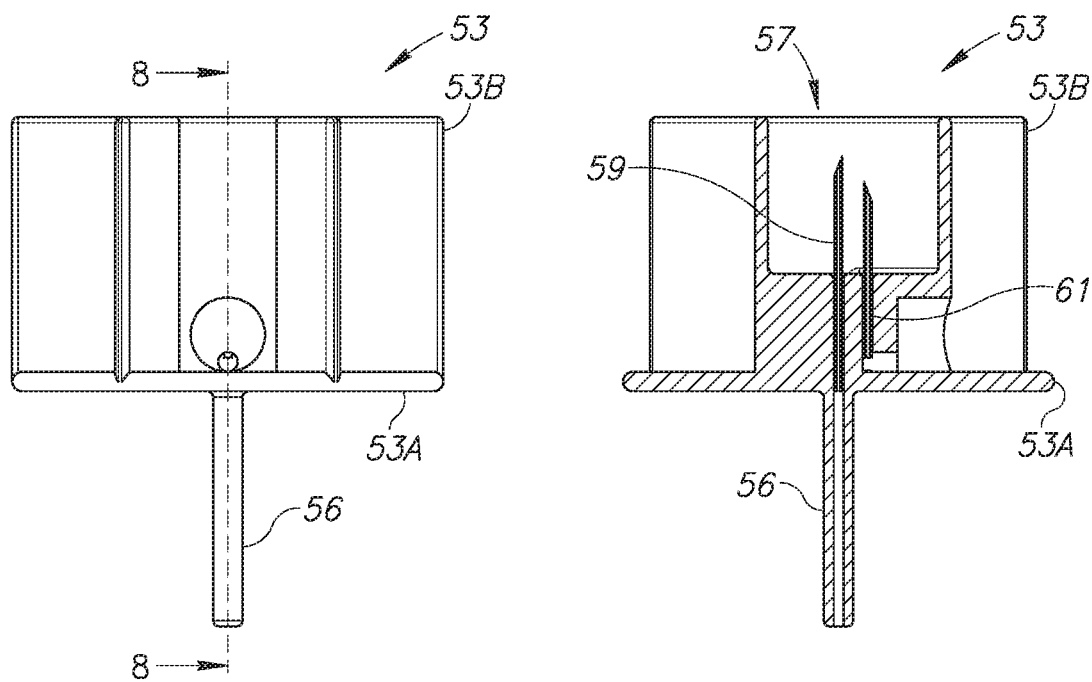
FIG. 7
FIG. 8

FLUID TRANSFER DEVICES FOR FILLING DRUG PUMP CARTRIDGES WITH LIQUID DRUG CONTENTS

CROSS-REFERENCE TO RELATED APPLICATIONS

This application is a Section 371 of International Application No. PCT/IL2017/050624, filed Jun. 5, 2017, which was published in the English language on Dec. 14, 2017 under International Publication No. WO 2017/212480 A1, and which claims priority under 35 U.S.C. § 119(b) to Israeli Patent Application No. 246073, filed Jun. 6, 2016, the disclosures of which are incorporated herein by reference.

FIELD OF THE INVENTION

The invention relates to fluid transfer devices for filling a drug pump cartridge with liquid drug contents.

BACKGROUND OF THE INVENTION

Drug pumps for self-administration of liquid drugs typically employ so-called drug pump carpules or cartridges including an open ended cartridge tube hermetically sealed by a cartridge septum at a leading cartridge end and a slidable driving plunger at an opposite trailing cartridge end. Drug pump cartridges are not pre-filled with liquid drug contents ready for immediate administration but are supplied either empty or pre-filled with diluent for reconstitution or dilution purposes. Accordingly, drug pump cartridges are required to be filled with liquid drug contents prior to being inserted into a drug pump.

Drug pumps are necessarily calibrated to take into account the static and dynamic frictional properties of a drug pump cartridge's slidable driving plunger. But displacement of a slidable driving plunger during a liquid drug filling procedure for filling a drug pump cartridge with liquid drug contents considerably changes its static and dynamic frictional properties. Moreover, drug pump cartridges have a relatively large variance in their frictional properties after displacement of their slidable driving plungers. Accordingly, a drug pump cartridge is preferably supplied with its slidable driving plunger sealingly enclosing a maximum dosage volume equal to or greater than a required dosage volume of liquid drug contents for administration purposes without displacement of its slidable driving plunger thereby affording reliable calibrated operation of a drug pump.

Commonly owned PCT International Application No. PCT/IL2007/000343 entitled Fluid Transfer Devices For Use With Cartridges published as PCT International Publication No. WO 2007/105221 discloses fluid transfer devices requiring the use of a needleless syringe for filling a drug pump cartridge without displacement of its slidable driving plunger thereby affording reliable calibrated operation of a drug pump.

Commonly owned PCT International Application No. PCT/IL2011/000530 entitled Fluid Transfer Devices For Filling a Cartridge with Liquid Drug Dosage published as PCT International Publication No. WO 2011/004360 discloses fluid transfer devices not requiring the use of a syringe for filling a drug pump cartridge but displacing its slidable driving plunger thereby precluding reliable calibrated operation of a drug pump.

Similarly, U.S. Pat. No. 6,752,180 to Delay entitled Device for Bidirectional Transfer of a Liquid Between a Vial and a Carpule discloses a fluid transfer device also displacing a drug pump cartridge's slidable driving plunger thereby precluding reliable calibrated operation of a drug pump. There is a need for fluid transfer devices for filling a drug pump cartridge without displacing its slidable driving plunger for reliable calibrated operation of a drug pump.

SUMMARY OF THE INVENTION

Generally speaking, the present invention is directed towards fluid transfer devices for filling a drug pump cartridge with liquid drug contents for administration purposes. The dosage volume of liquid drug contents is known before filling a drug pump cartridge and therefore the drug pump cartridge can be supplied with its slidable driving plunger sealingly enclosing a maximum dosage volume equal to or greater than the dosage volume of liquid drug contents such that it can be filled without displacing its slidable driving plunger thereby ensuring reliable calibrated operation of a drug pump. The fluid transfer devices of the present invention can be classified into two types as follows: First, transferring liquid drug contents ready for administration from a drug vial to fill an initially empty drug pump cartridge. And second, transferring liquid contents from an initially pre-filled drug pump cartridge to a drug vial for forming liquid drug contents therein and thereafter transferring the liquid drug contents from the drug vial to the drug pump cartridge. The latter type is necessarily used with drug vials under negative pressure for enabling positive drawing of liquid contents from an initially pre-filled drug pump cartridge into a drug vial for reconstitution or dilution purposes.

The first type of fluid transfer device has a longitudinal fluid transfer device centerline and includes a dual open ended barrel partitioned by a transverse partition into a drug vial port for telescopic mounting on a drug vial and an open ended piston cylinder for slidingly receiving a piston head including a drug pump cartridge port for telescopic mounting on a leading cartridge end of a drug pump cartridge. On assembly, the drug vial is in continuous liquid flow communication with the drug pump cartridge. The drug pump cartridge is vented. The piston head is initially spaced apart from the transverse partition to seal a compression chamber. Sliding insertion of the piston head into the piston cylinder to butt against the transverse partition urges air trapped in the compression chamber into the drug vial which in turn urges its liquid drug contents into the vented drug pump cartridge.

The second type of fluid transfer device is similar to the first type and additionally includes a manual operated flow control arrangement for selectively opening and closing flow communication between a drug vial and a compression chamber for enabling positive drawing of liquid contents from an initially pre-filled drug pump cartridge into a drug vial.

BRIEF DESCRIPTION OF DRAWINGS

In order to understand the invention and to see how it can be carried out in practice, preferred embodiments will now be described, by way of non-limiting examples only, with reference to the accompanying drawings in which similar parts are likewise numbered, and in which:

FIG. 6 is a front perspective view of the piston head;

FIG. 7 is a front elevation view of the piston head;

FIG. 8 is a longitudinal cross section of the piston head along line 8-8 in FIG. 7;

DETAILED DESCRIPTION OF PREFERRED EMBODIMENTS OF THE INVENTION

Figure 1:
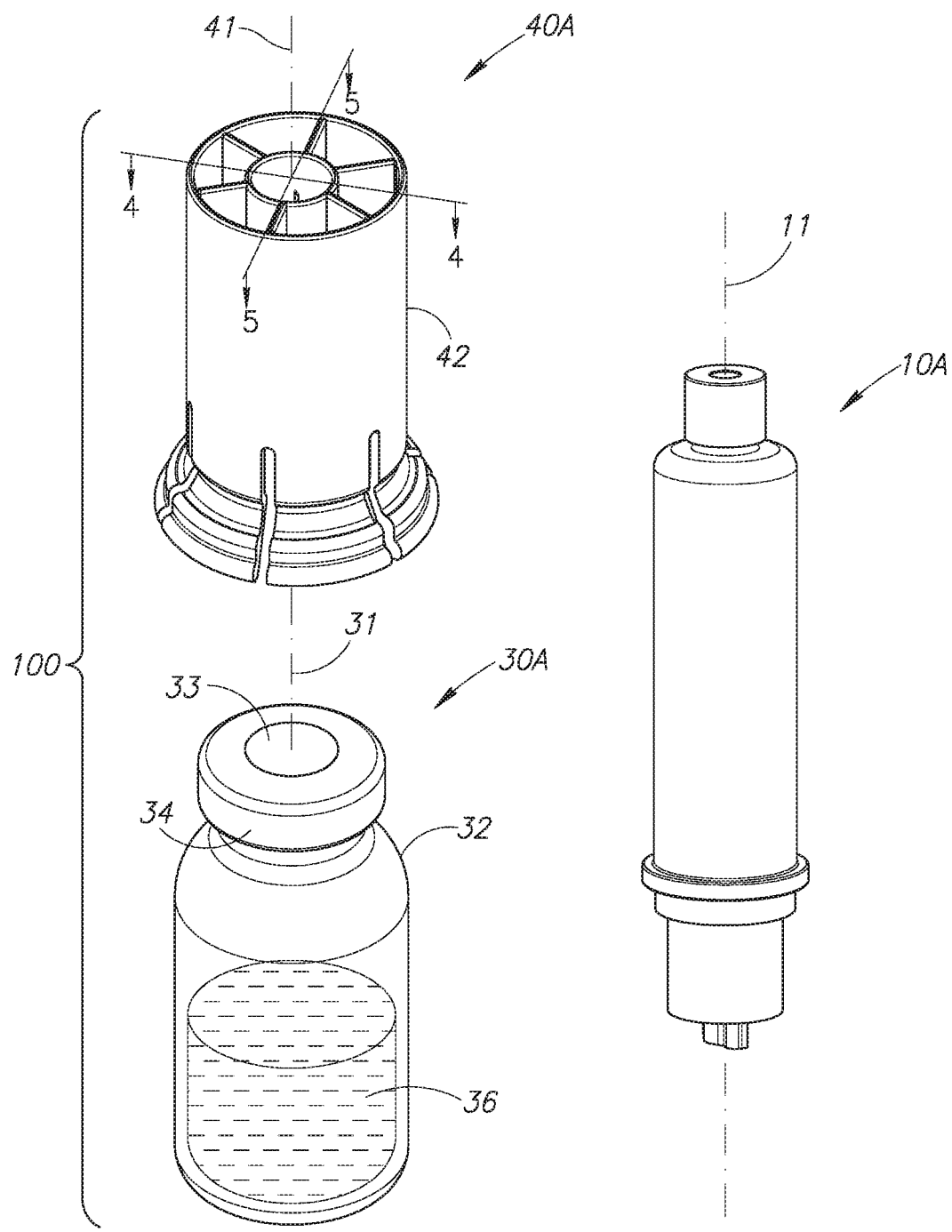
FIG. 1 is a pictorial representation of a kit including a drug pump cartridge, a drug vial and a fluid transfer device in accordance with a first preferred embodiment of the present invention.

Transfer of Liquid Drug Contents from Drug Vial to Initially Empty Drug Pump Cartridge FIG. 1 shows a kit 100 including an initially empty drug pump cartridge 10A, a drug vial 30A containing liquid drug contents and a fluid transfer device 40A for transferring the liquid drug contents from the drug vial 30A to the drug pump cartridge 10A. The fluid transfer device 40A has a longitudinal fluid transfer device centerline 41 and includes a dual open ended barrel 42.

Figure 2:
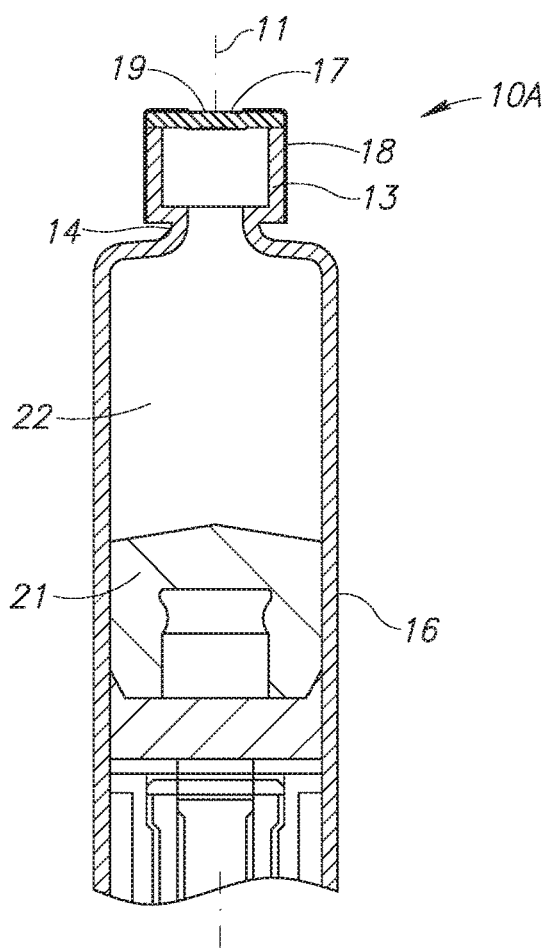
FIG. 2 is a longitudinal cross section of the drug pump cartridge.
Figure 3:
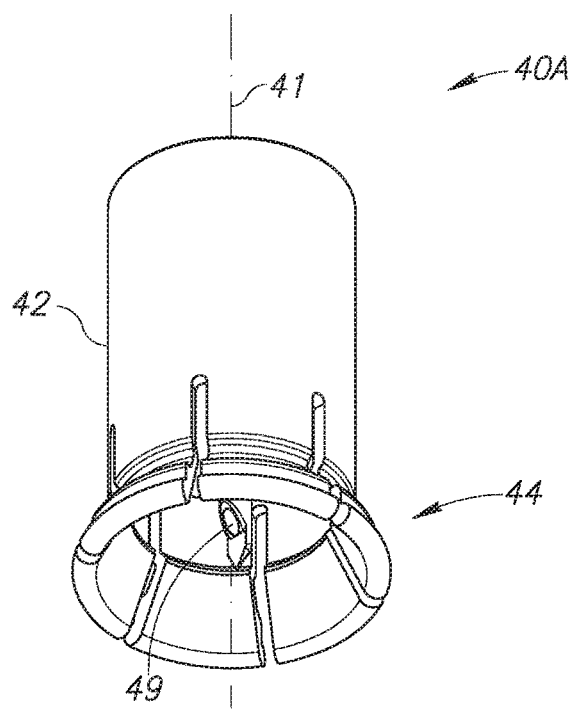
FIG. 3 is a bottom perspective view of the FIG. 1 fluid transfer device.
Figure 4:
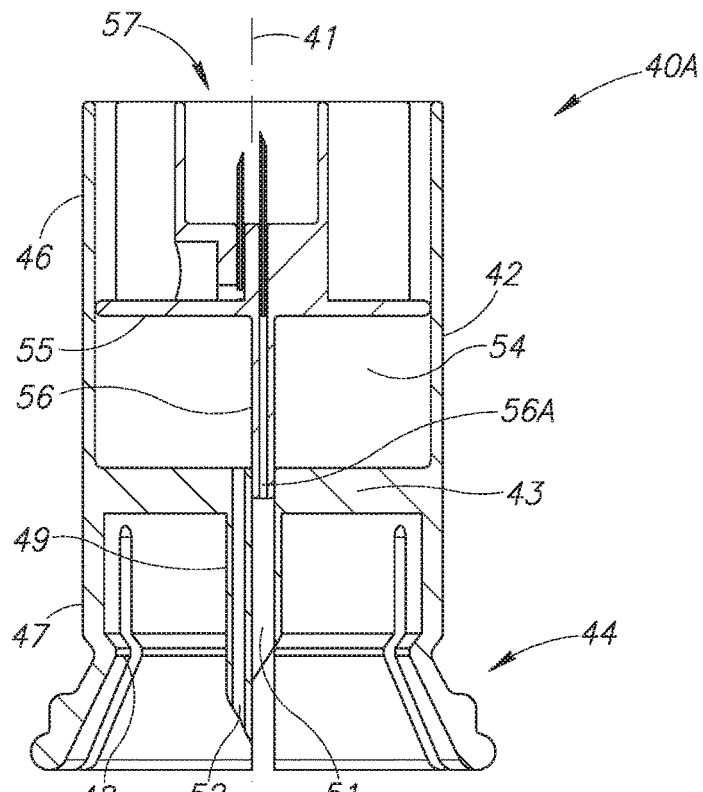
FIG. 4 is a longitudinal cross section of the FIG. 1 fluid transfer device in its initial set-up position along line 4-4 in FIG. 1.
Figure 5:
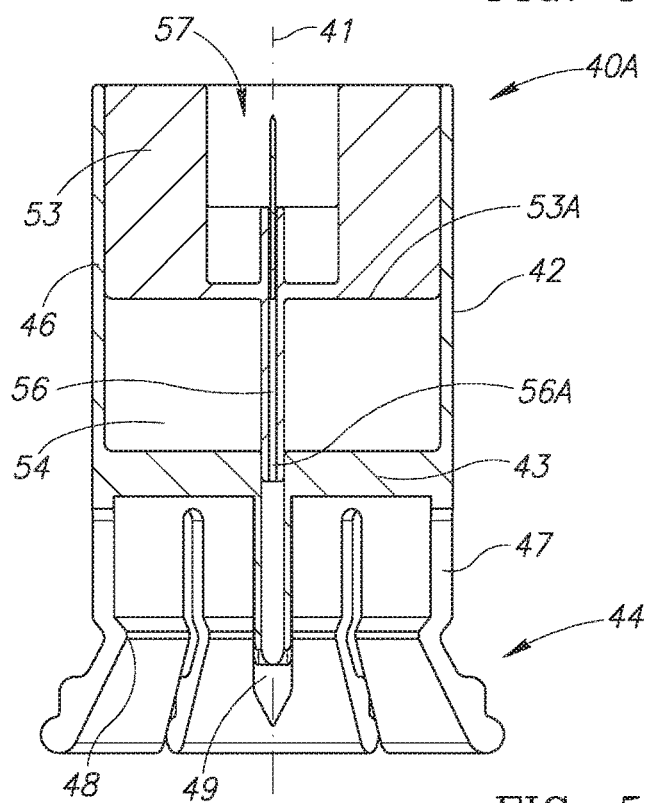
FIG. 5 is a longitudinal cross section of the FIG. 1 fluid transfer device in its initial set-up position along line 5-5 of FIG. 1.

FIG. 2 shows the drug pump cartridge 10A has a longitudinal drug pump cartridge centerline 11 and includes an open ended cartridge tube 12, a small diameter leading cartridge end 13, an intermediate neck 14 and a wide diameter trailing cartridge end 16. The leading cartridge end 13 is hermetically sealed by a cartridge septum 17 capped by a metal band 18. The leading cartridge end 13 has an exposed 2 mm to 3 mm diameter circular septum surface 19. The trailing cartridge end 16 is hermetically sealed by a slidable driving plunger 21 for bounding a cartridge chamber 22 of variable volume from zero when the slidable driving plunger 21 is fully inserted and abutting against the leading cartridge end 13 to a maximal dosage volume V1.

FIG. 1 shows the drug vial 30A has a longitudinal drug vial centerline 31 and includes an open topped vial bottle 32 initially hermetically sealed by a drug vial stopper 33 capped by a metal band 34. The drug vial 30A contains a known dosage volume V2 of liquid drug contents 36 for administration purposes. The liquid drug contents 36 can be prepared by means of a conventional female drug vial adapter and a needleless syringe containing diluent or active liquid compound.

Turning now to FIG. 3 to FIG. 8, the dual open ended barrel 42 includes a transverse partition 43 partitioning same into a drug vial port 44 for telescopically mounting on a drug vial 30A and an open ended piston cylinder 46. The drug vial port 44 includes flex members 47 with inwardly directed protrusions 48 for conventional snap fit on a drug vial 30A. The transverse partition 43 is formed with a longitudinal central dual lumen puncturing cannula 49 extending into the drug vial port 44 for puncturing a drug vial stopper 33 on telescopic mounting the fluid transfer device 40A on a drug vial 30A. The dual lumen puncturing cannula 49 includes a liquid lumen 51 and an air lumen 52. The liquid lumen 51 has a greater lumen diameter than the air lumen 52.

The fluid transfer device 40A includes a piston head 53 having a leading piston head end 53A and a trailing piston head end 53B. The piston head 53 is slidingly inserted into the piston cylinder 46 such that the leading piston head end 53A bounds a compression chamber 54 with the transverse partition 43. The piston head 53 is formed with a longitudinal transfer tube 56 for extending through the compression chamber 54 and shaped and dimensioned for sealing sliding insertion in the liquid lumen 51. The transfer tube 56 includes a transfer tube tip 56A inserted in the liquid lumen 51 in the initial set-up position of the fluid transfer device 40A.

The piston head 53 is formed with a drug pump cartridge port 57 remote from the transverse partition 43 for snugly mounting on a leading cartridge end 13. The drug pump cartridge port 57 is formed with radial directed vanes 58 for stabilizing displacement of the piston head 53 in the piston cylinder 46. The drug pump cartridge port 57 is formed with a puncturing cannula 59 for puncturing a cartridge septum 17 on sliding insertion of a leading cartridge end 13 therein. The puncturing cannula 59 is in flow communication with the transfer tube 56 such that the puncturing cannula 59 is in flow communication with the liquid lumen 51. The drug pump cartridge port 57 is formed with a vented puncturing cannula 61 for puncturing a cartridge septum 17 on sliding insertion of a leading cartridge end 13 therein. The vented puncturing cannula 61 is vented between adjacent vanes 58.

The fluid transfer device 40A is designed such that on telescopic mounting the fluid transfer device 40A on a drug pump cartridge 10A, the drug pump cartridge port 57 punctures a cartridge septum 17 before the piston head 53 starts sliding in the piston cylinder 46.

Figure 9A:
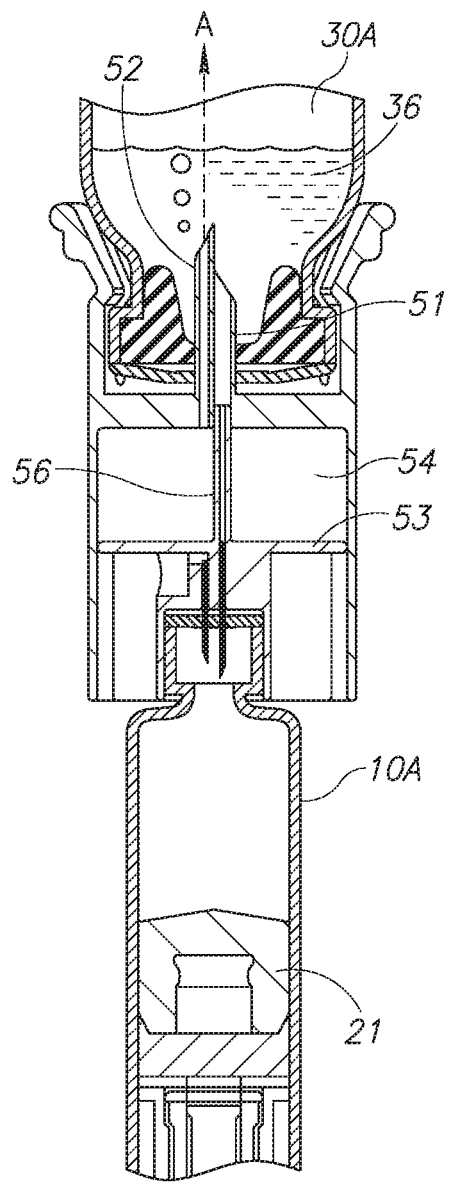
FIG. 9A is a longitudinal cross section of a fluid transfer assemblage including the FIG. 1 fluid transfer device, a drug vial and a drug pump cartridge before transferring liquid drug contents to the drug pump cartridge.

FIG. 9A and FIG. 9A show two operative positions of the fluid transfer device 40A as follows:

FIG. 9A shows an initial set-up position in which the drug vial port 44 is telescopically mounted on an initially full drug vial 30A, the drug pump cartridge port 57 is telescopically mounted on an initially empty drug pump cartridge 10A and the piston head 53 is spaced apart from the transverse partition 43. The transfer tube tip 56A is in the liquid lumen 51. The compression chamber 54 contains trapped air.

Figure 9B:
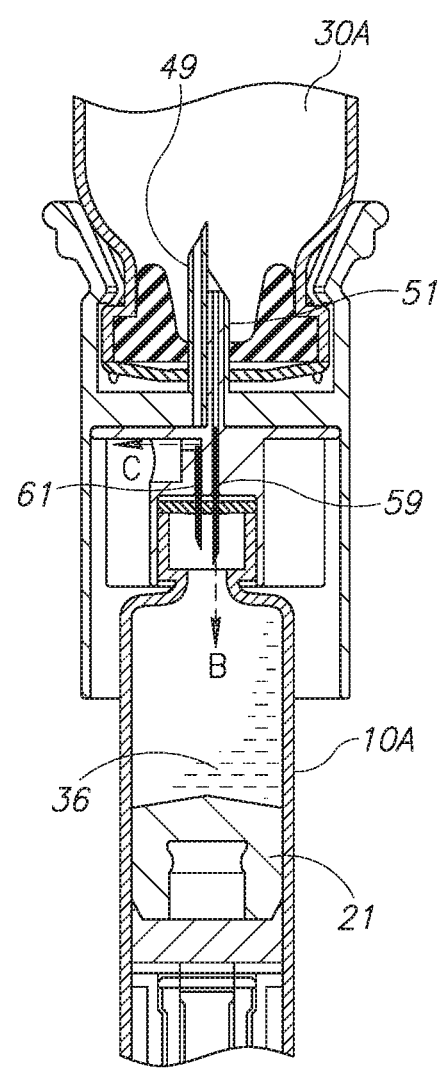
FIG. 9B is a longitudinal cross section of a fluid transfer assemblage including the FIG. 1 fluid transfer device, a drug vial and a drug pump cartridge after transferring liquid drug contents to the drug pump cartridge.

FIG. 9B shows a final filling position in which the piston head 53 abuts against the transverse partition 43 and the transfer tube 56 is near entirely inserted in the liquid lumen 51. The sliding insertion of the piston head 53 into the piston cylinder 46 urges the trapped air in the compression chamber 54 into the drug vial 30A as denoted by arrow A in FIG. 9A. The urging of the trapped air into the drug vial 30A in turn urges the liquid drug contents 36 from the drug vial 30A into the drug pump cartridge 10A as denoted by arrow B. The urging of the liquid drug contents 36 into the drug pump cartridge 10A expels air through the vented puncturing cannula 61 as denoted by arrow C. The slidable driver plunger 21 remains at the same displacement from the cartridge septum 17 during the filling procedure.

FIG. 10A to FIG. 10D show use of the kit 100 for transferring liquid drug contents 36 from a drug vial 30A into an initially empty drug pump cartridge 10A. The drug pump cartridge 10A is supplied with its slidable driving plunger 21 initially spaced apart from the cartridge septum 17 for sealing the cartridge chamber 22 with a maximal dosage volume V1 equal to or greater than the known dosage volume V2 in order not to displace the slidable driving plunger 21 from its initial position during filling the drug pump cartridge 10A. In the case V1=V2, the cartridge chamber 22 is completely filled by the liquid drug contents 36 such that liquid drug contents are immediately pumped from the drug pump cartridge 10A on operation of a drug pump. In the case V1>V2, the cartridge chamber 22 is partially filled by the liquid drug contents 36 such that a drug pump initially bleeds air from the drug pump cartridge 10A before pumping liquid drug contents therefrom. FIG. 10A to FIG. 10D show use of the kit 100 for transferring liquid drug contents in the case the maximal dosage volume V1 and the dosage volume V2 are equal.

Figure 10D:
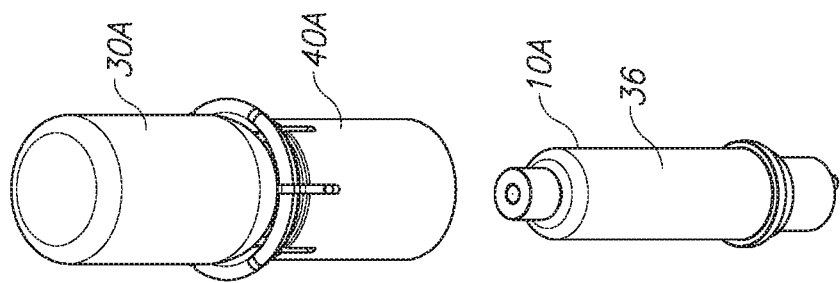
FIG. 10A to FIG. 10D show use of the FIG. 1 kit for filling the drug pump cartridge with liquid drug contents ready for administration to a patient.
Figure 10C:
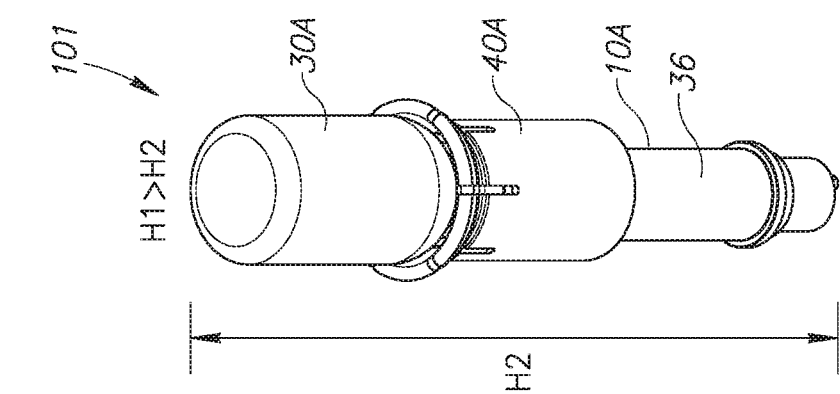
Figure 10B:
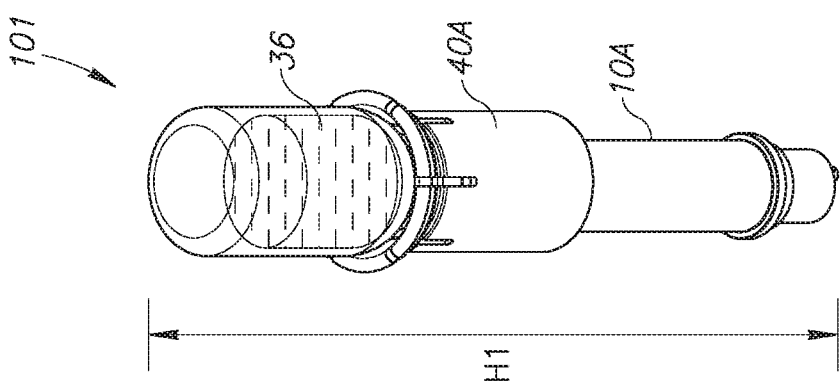
Figure 10A:
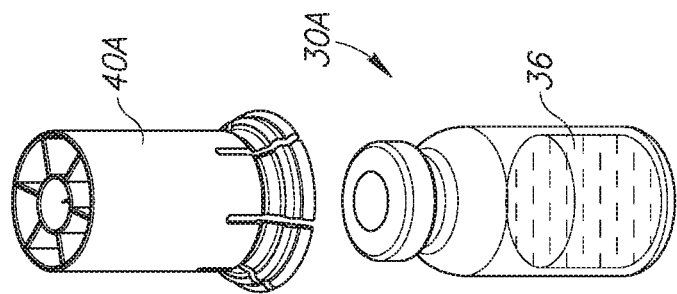

FIG. 10A shows telescopically mounting the fluid transfer device 40A on the drug vial 30A for puncturing same. Both the liquid lumen 51 and the air lumen 52 are in flow communication with the drug vial bottle 32.

FIG. 10B and FIG. 10C show inverting the fluid transfer device 40A and the drug vial 30A and a single continuous insertion stroke for mounting the fluid transfer device 40A on the drug pump cartridge 10A to transfer the liquid drug contents 36 from the drug vial 30A to the drug pump cartridge 10A. The single continuous insertion stroke effectively performs two consecutive actions as follows:

FIG. 10B shows the drug pump cartridge port 57 telescopically mounting on the leading cartridge end 13 to form a fluid transfer assemblage 101. Both the puncturing cannula 59 and the vented puncturing cannula 61 puncture the cartridge septum 17 to be in flow communication with the cartridge chamber 22. The fluid transfer assemblage 101 has an initial set-up height H1.

FIG. 10C shows the piston head 53 fully inserted into the piston cylinder 46 for abutting against the transverse partition 43 for transferring the liquid drug contents 36 from the drug vial 30A to the drug pump cartridge 10A without displacing the slidable driving plunger 21. The fluid transfer assemblage 101 is compacted by the length of the insertion stroke to a final filling height H2 where H1>H2.

FIG. 10D shows detachment of the now filled drug pump cartridge 10A from the fluid transfer device 40A for insertion into a drug pump for administration of the liquid drug contents 36 to a patient. The fluid transfer device 40A and the now empty drug vial 30A can be discarded.

Figure 11:
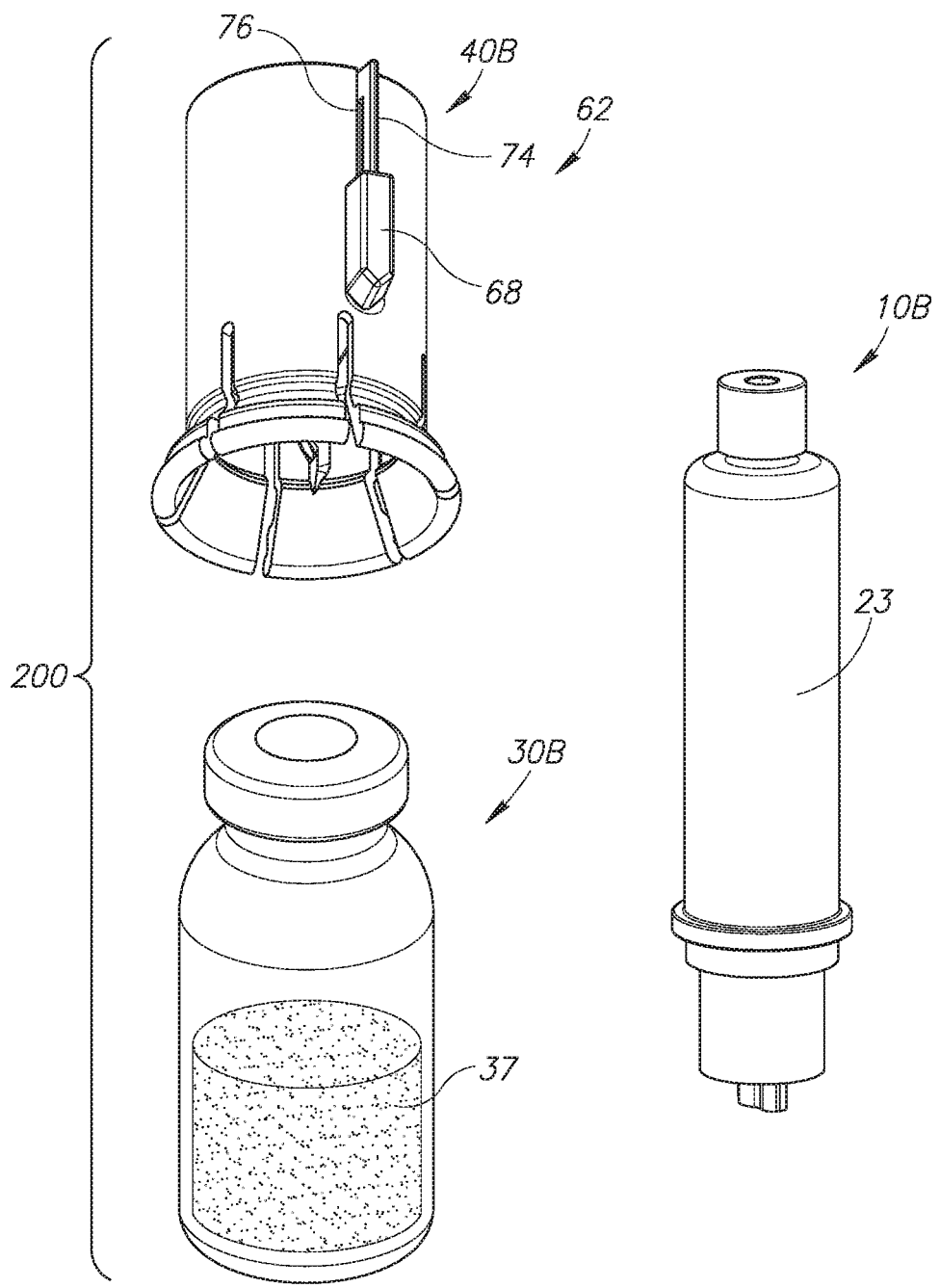
FIG. 11 is a pictorial representation of a kit including a drug pump cartridge, a drug vial and a fluid transfer device including a manual operated flow control arrangement in accordance with a second preferred embodiment of the present invention.
Figure 12:
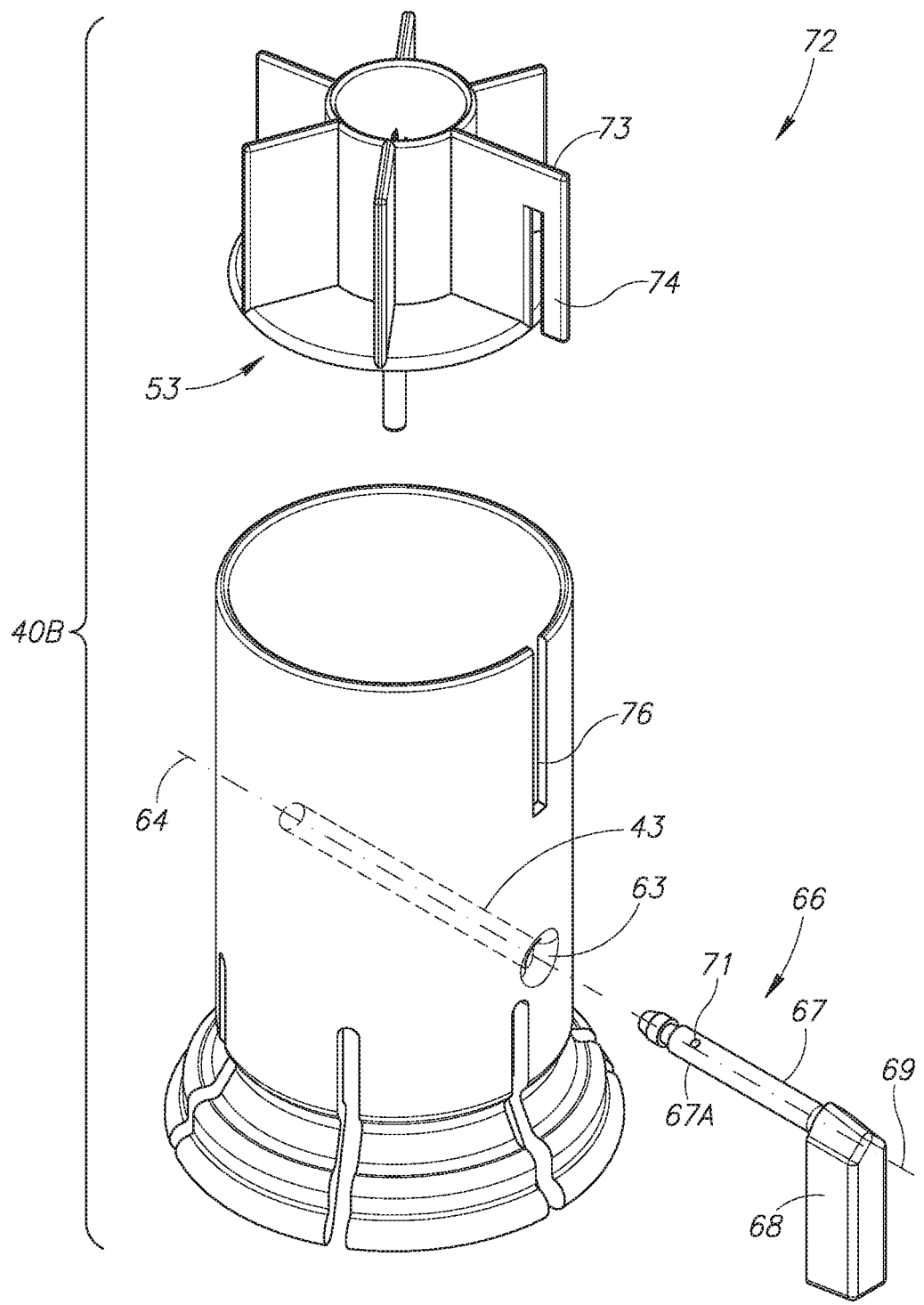
FIG. 12 is an exploded view of the FIG. 11 fluid transfer device.
Figure 13:
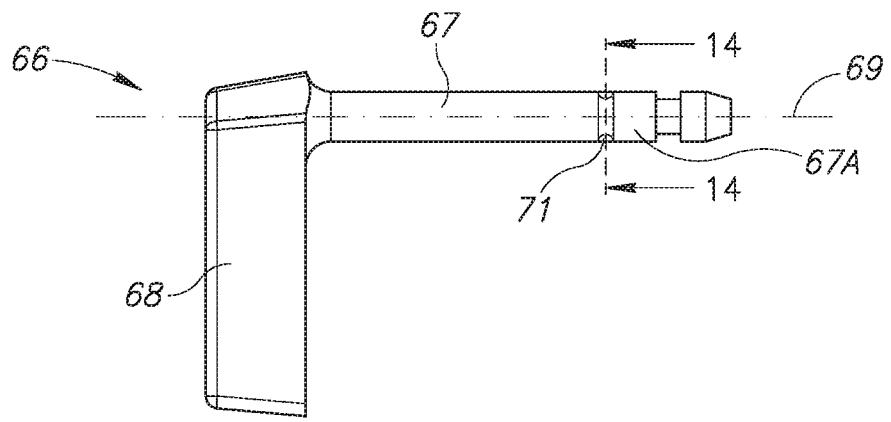
FIG. 13 is a front elevation view of a L-shaped flow control member of the manual operated flow control arrangement.
Figure 14:
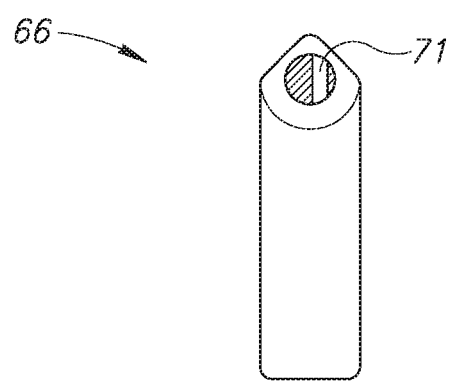
FIG. 14 is a transverse cross section of the L-shaped flow control member along line 14-14 in FIG. 13.

Transfer of Liquid Contents from Pre-Filled Drug Pump Cartridge to Drug Vial for Forming Liquid Drug Contents Therein and Subsequent Transfer of Liquid Drug Contents from Drug Vial to Drug Pump Cartridge FIG. 11 shows a kit 200 including a pre-filled drug pump cartridge 10B, a drug vial 30B and a fluid transfer device 40B for filling the drug pump cartridge 10B with liquid drug contents. The drug pump cartridge 10B is pre-filled with liquid contents 23 in the form of diluent or an active liquid component. The drug vial 30B is necessarily under negative pressure and contains a medicament 37 in the form of a powder or a liquid. The fluid transfer device 40B is similar to the fluid transfer device 40A and differs therefrom in two respects: First, the fluid transfer device 40B includes a manual operated flow control arrangement 62 for initially closing the air lumen 52 and selectively opening the air lumen 52 for correspondingly enabling initial positive drawing liquid contents from the drug pump cartridge 10B into the drug vial 30B for initially preparing liquid drug contents 36 therein and subsequent transfer of the liquid drug contents 36 from the drug vial 30B to the drug pump cartridge 10B. And second, the fluid transfer device 40B preferably precludes an inadvertent insertion stroke of the piston head 53 until after the positive drawing the liquid contents from the drug pump cartridge 10B into the drug vial 30B.

The fluid transfer device 40B includes a transverse directed blind bore 63 in the transverse partition 43 to intersect the air lumen 52. The blind bore 63 has a blind bore centerline 64 perpendicular to the fluid transfer device centerline 41. The flow control arrangement 62 includes a manual rotated L-shaped flow control member 66 having a flow control member shank 67 and a flow control member handle 68. The flow control member shank 67 extends into the blind bore 63 and is rotatable about a rotation axis 69 coinciding with the blind bore centerline 64. The flow control member handle 68 is flush with the dual open ended barrel 42. The flow control member shank 67 has a leading flow control member shank end 67A which intersects the air lumen 52. The leading flow control member shank end 67A is formed with a throughgoing bore 71 off-set from the rotation axis 69.

The trailing piston head end 53B is formed with a L-shaped stop member 72 including a transverse mirror L-shaped stop member leg 73 and a longitudinal major L-shaped stop member leg 74 directed towards the leading piston head end 53A. The piston cylinder 46 is formed a longitudinal directed slit 76 extending the length of the insertion stroke of the piston head 53 into the piston cylinder 46.

Figure 15A:
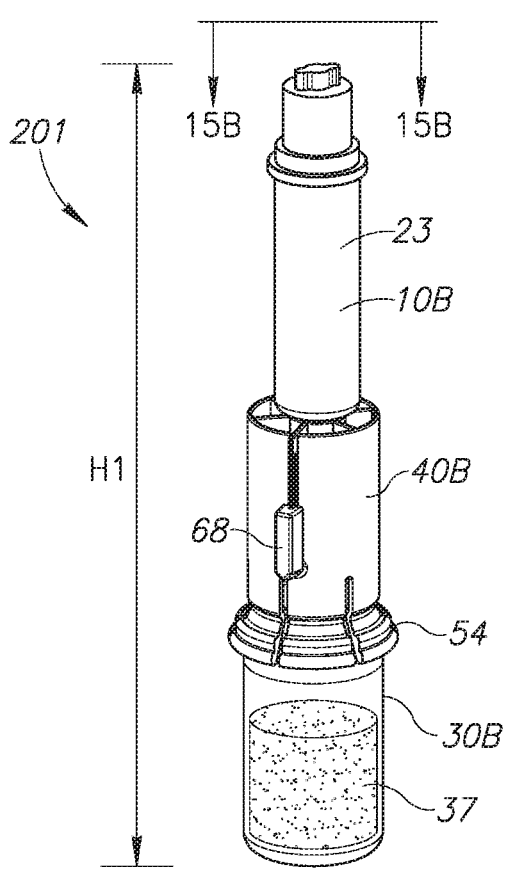
FIG. 15A is a side elevation view of a fluid transfer assemblage including the FIG. 11 fluid transfer device with the flow control arrangement in an initial closed state, a drug vial and a drug pump cartridge for drawing liquid contents from the drug pump cartridge to the drug vial.
Figure 15B:
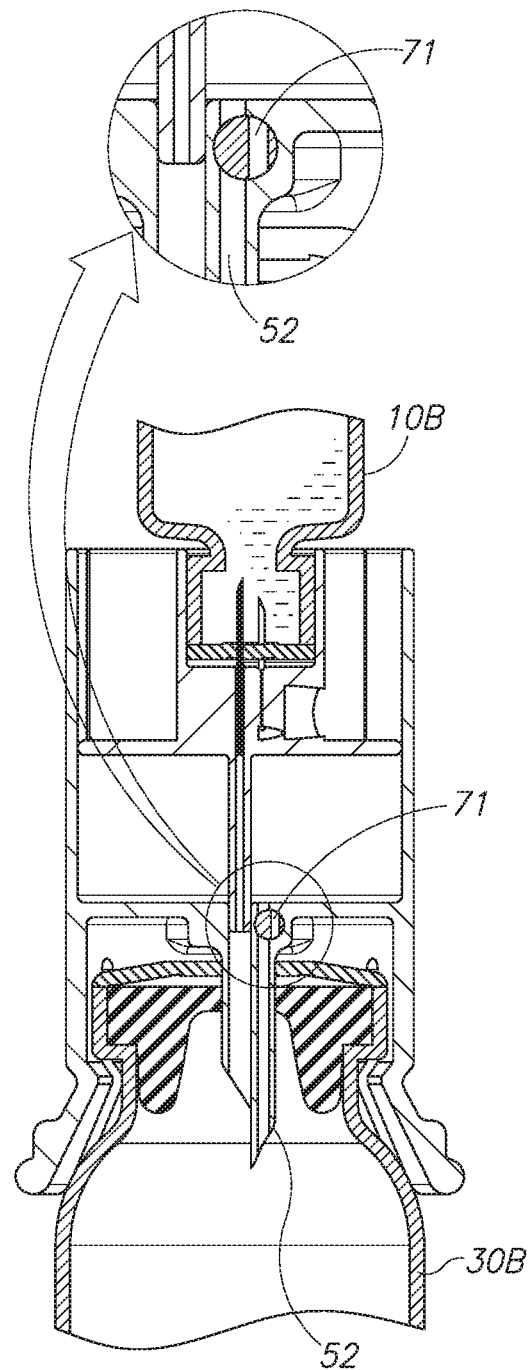
FIG. 15B is a longitudinal cross section of the FIG. 15A fluid transfer assemblage along line 15B-15B in FIG. 15A.

FIG. 15A and FIG. 15B show the flow control arrangement 62 in an initial closed state for closing the air lumen 52. The fluid transfer device 40B is designed such that the major L-shaped stop member 74 and the flow control member handle 68 abut in the initial closed state for precluding an inadvertent insertion stroke of the piston head 53 into the piston cylinder 46 before transferring liquid contents 23 from the drug pump cartridge 10B to the drug vial 30B for forming liquid drug contents 36 therein.

Figures 16A, 16B:
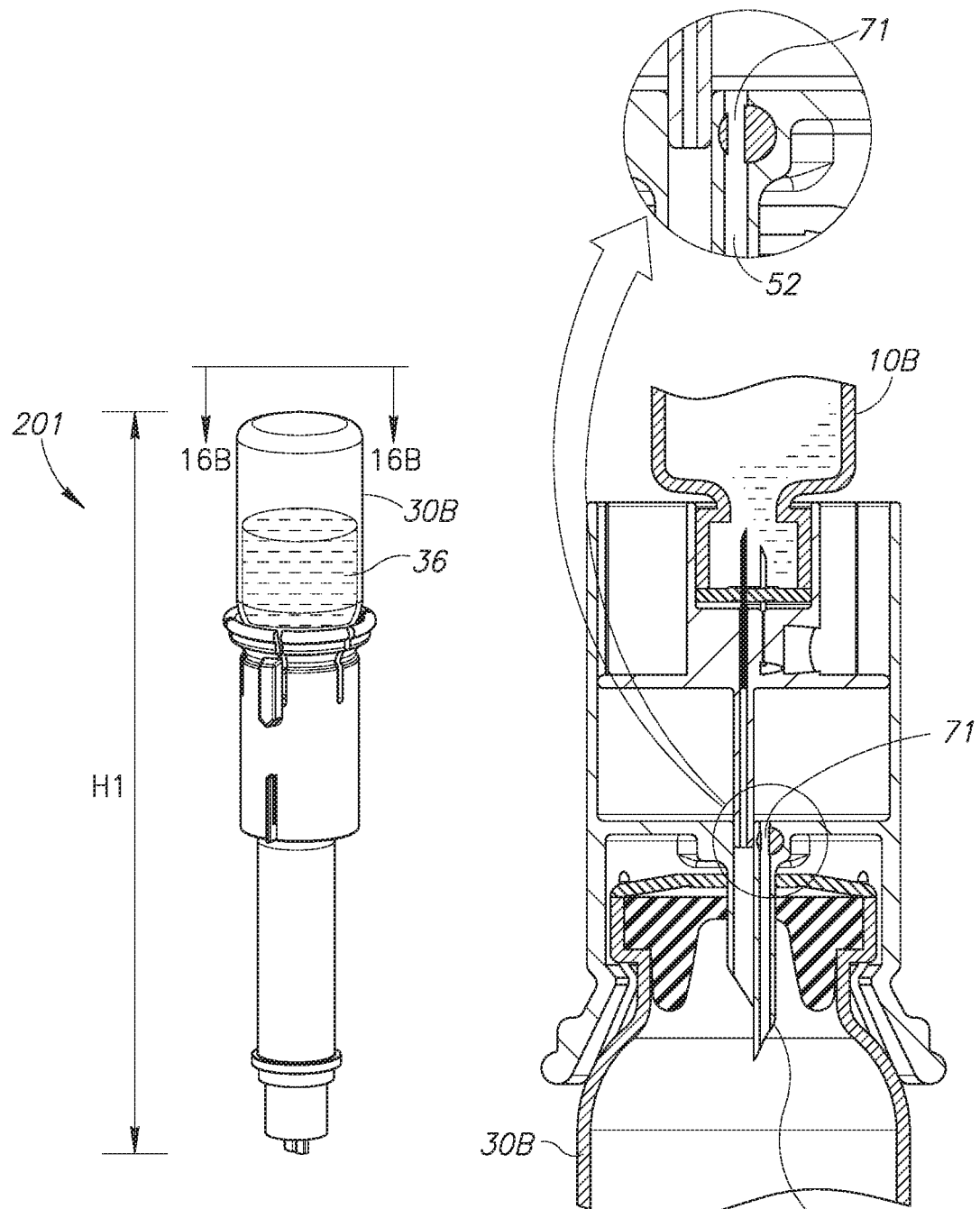
FIG. 16A is a side elevation view of a fluid transfer assemblage including the FIG. 11 fluid transfer device with the flow control arrangement in a final open state, a drug vial and a drug pump cartridge ready for transferring liquid drug contents from the drug vial to the drug pump cartridge.
FIG. 16B is a longitudinal cross section of the FIG. 16A fluid transfer assemblage along line 16B-16B in FIG. 16A.

FIG. 16A and FIG. 16B show the flow control arrangement 62 in a final open state for opening the air lumen 52 by half turn rotation of the flow control member handle 68 which additionally enables the insertion stroke of the piston head 53 into the piston cylinder 46.

FIG. 17A to FIG. 17E show use of the kit 200 for the case the maximal dosage volume V1 and the dosage volume V2 of liquid drug contents 36 for administration purposes are equal. The fluid transfer device 40B is in its initial set-up state with the flow control member 66 closing the air lumen 52 and the piston head 53 spaced apart from the transverse partition 43 ready for its insertion stroke theretowards.

Figure 17C:
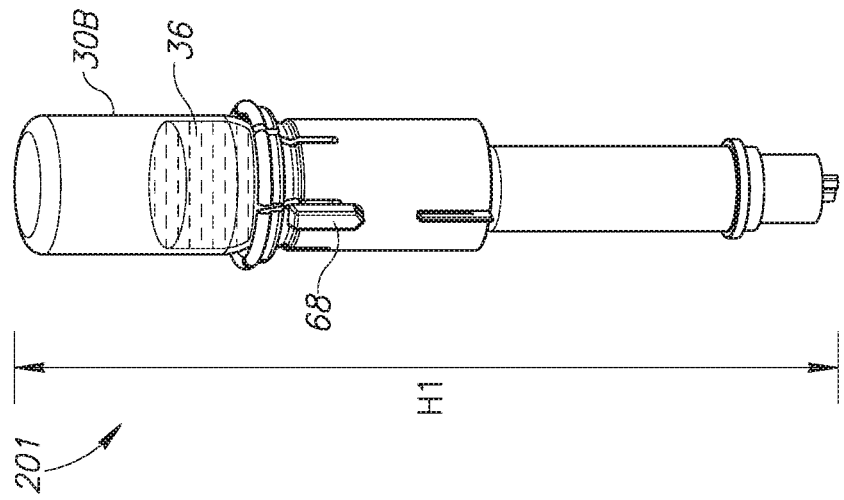
FIG. 17A to FIG. 17E show use of the FIG. 11 kit for filling the drug pump cartridge with liquid drug contents ready for administration to a patient.
Figure 17B:
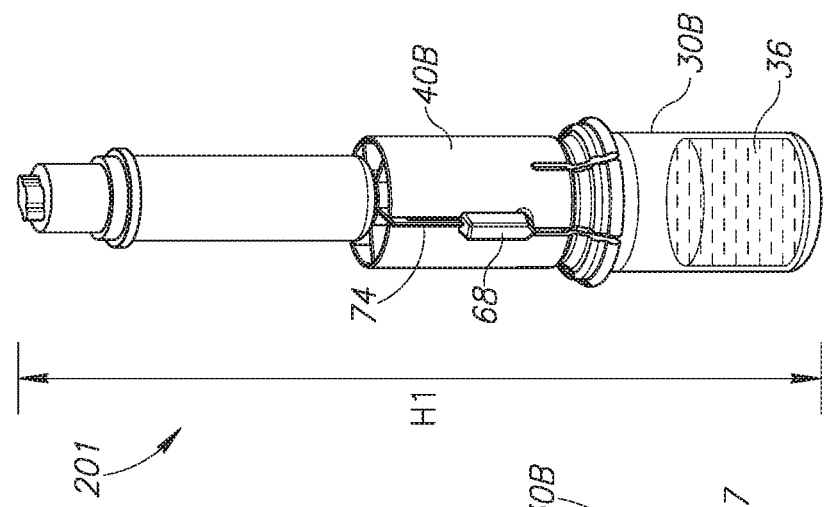
Figure 17A:
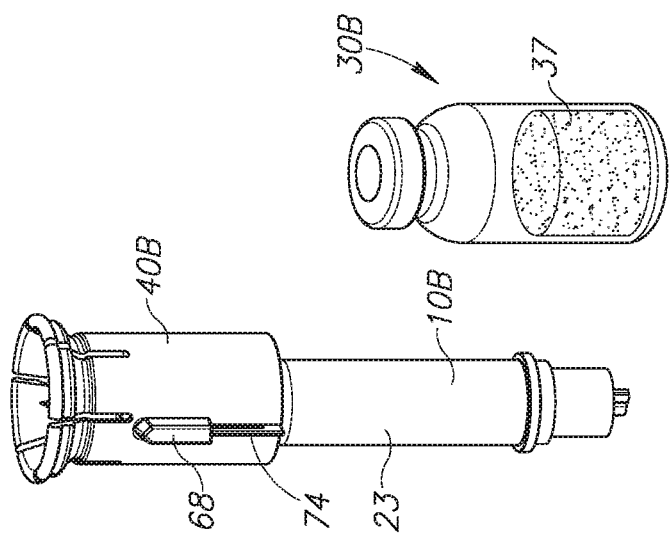

FIG. 17A shows telescopically mounting the fluid transfer device 40B on the drug pump cartridge 10B for puncturing same.

FIG. 17B shows inverting the fluid transfer device 40B and the drug pump cartridge 10B for telescopic mounting on the drug vial 30B to transfer the liquid contents 23 from the drug pump cartridge 10B to the drug vial 30B as facilitated by the venting of the drug pump cartridge 10B. The liquid contents 23 reconstitute the powder medicament 37 to form the dosage volume V2 of liquid drug contents 36. The drug pump cartridge 10B, the drug vial 30B and the fluid transfer device 40B form a fluid transfer assemblage 201 having an initial set-up height H1.

FIG. 17C shows inverting the fluid transfer assemblage 201 and half turn rotation of the flow control member handle 68 for opening the air lumen 52.

Figure 17E:
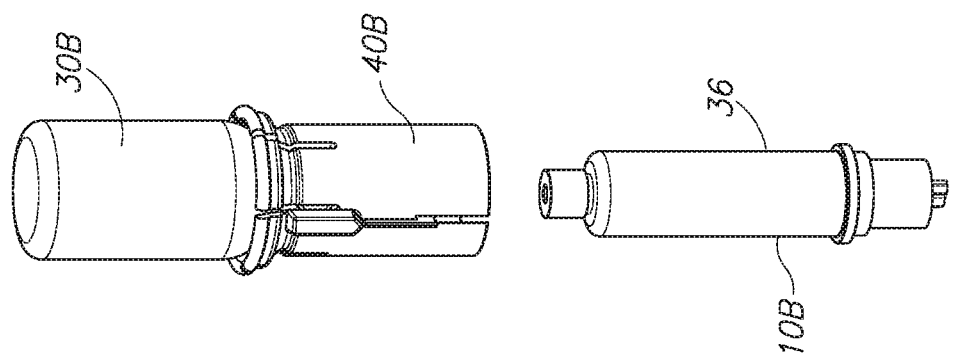
Figure 17D:
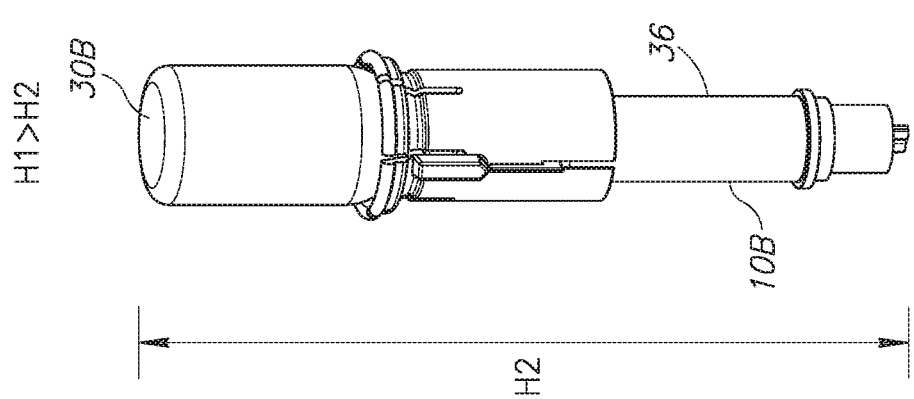

FIG. 17D shows the fluid transfer assemblage 201 after the insertion stroke of the piston head 53 into the piston cylinder 46 for transferring the liquid drug contents 36 from the drug vial 30B to the drug pump cartridge 10B without displacing the slidable driving plunger 21 in a similar manner to the fluid transfer assemblage 101. The fluid transfer assemblage 201 is compacted to a final filling height H2 where H1>H2.

FIG. 17E shows detachment of the now filled drug pump cartridge 10B from the fluid transfer device 40B for insertion into a drug pump for administration of the liquid drug contents 36 to a patient. The fluid transfer device 40B and the now empty drug vial 30B can be discarded.

While the invention has been described with respect to a limited number of embodiments, it will be appreciated that many variations, modifications, and other applications of the invention can be made within the scope of the appended claims.

The invention claimed is:

1. A fluid transfer device for use with a drug vial and a drug pump cartridge for transferring liquid drug contents from the drug vial to the drug pump cartridge,
   the drug vial having an open topped drug vial bottle sealed by a drug vial stopper and containing a dosage volume of liquid drug contents for administration purposes,
   the drug pump cartridge having an open ended cartridge tube having a leading cartridge end, a cartridge septum sealing the leading cartridge end, a slidable driving plunger distanced from the cartridge septum for sealing a maximal dosage volume equal to or greater than the dosage volume of liquid drug contents,
   the fluid transfer device comprising:
   (a) a dual open ended barrel having a longitudinal barrel centerline and a transverse partition partitioning said dual open ended barrel into a drug vial port for telescopically mounting on the drug vial and an open ended piston cylinder,
   said partition having a dual lumen drug vial stopper puncturing cannula extending into said drug vial port for puncturing the drug vial stopper on said telescopic mounting said drug vial port on the drug vial,
   said dual lumen drug vial stopper puncturing member including a liquid lumen and an air lumen; and
   (b) a piston head slidingly mounted in said open ended piston cylinder to seal a compression chamber with said transverse partition,
   said compression chamber being in flow communication with said air lumen,
   said piston head having a drug pump cartridge port for telescopically mounting on the leading cartridge end,
   said drug pump cartridge port including a major cartridge septum puncturing cannula and a minor cartridge septum puncturing cannula for puncturing the cartridge septum on said telescopic mounting said drug pump cartridge port on the leading cartridge end,
   said major cartridge septum puncturing cannula being in sealed flow communication with said liquid lumen for liquid transfer between the drug vial and the drug pump cartridge,
   said minor cartridge septum puncturing cannula venting the drug pump cartridge on said telescopic mounting said drug pump cartridge port on the leading cartridge end,
   the fluid transfer device having an initial set-up position in which said piston head is spaced apart from said transverse partition for trapping air in said compression chamber and a final filling position in which said piston head is slidingly inserted towards said transverse partition along an insertion stroke for urging said trapped air into the drug vial for urging the drug vial's dosage volume of liquid drug contents into the drug pump cartridge without displacing the slidable driving plunger.

2. The device according to claim 1 for use with a drug vial under negative pressure and a pre-filled drug pump cartridge containing liquid contents and further comprising a manual operated flow control arrangement for selectively opening and closing said air lumen,
   said flow control arrangement having an initial closed state for closing said air lumen in said initial set-up position for enabling positive drawing of liquid contents from the drug pump cartridge to the drug vial on initial telescopic mounting said drug pump cartridge port on the leading cartridge end and subsequent telescopic mounting said drug vial port on the drug vial for forming the liquid drug contents in the drug vial, and
   said flow control arrangement having a subsequent open state for opening said air lumen for enabling urging of said trapped air from said compression chamber into the drug vial on said sliding insertion of said piston head in said piston cylinder from said initial set-up position to said final filling position for transferring the liquid drug contents from the drug vial to the vented drug pump cartridge.

3. The device according to claim 2 wherein said flow control arrangement includes a manual rotatable flow control member having a flow control member shank intersecting said air lumen and a flow control member handle for rotating said flow control member.

4. The device according to claim 3 wherein said piston head includes a stop member for abutting against said flow control member handle in said initial closed state for preventing said sliding insertion of said piston head into said open ended piston cylinder in said initial set-up position.

5. The device according to claim 1 wherein said transverse partition includes a transfer tube oppositely directed from said drug pump cartridge port for sliding insertion in said liquid lumen from an initial partial insertion in said initial set-up position.

* * * * *